(12) United States Patent
Holt

(10) Patent No.: US 9,632,073 B2
(45) Date of Patent: Apr. 25, 2017

(54) APPARATUS AND METHOD FOR MOLECULAR SEPARATION, PURIFICATION, AND SENSING

(75) Inventor: Gordon Holt, Beaverton, OR (US)

(73) Assignee: LUX BIO GROUP, INC., Camas, WA (US)

( * ) Notice: Subject to any disclaimer, the term of this patent is extended or adjusted under 35 U.S.C. 154(b) by 0 days.

(21) Appl. No.: 13/437,793

(22) Filed: Apr. 2, 2012

(65) Prior Publication Data

US 2013/0260472 A1 Oct. 3, 2013

(51) Int. Cl.

| | |
|---|---|
| *G01N 27/26* | (2006.01) |
| *G01N 27/00* | (2006.01) |
| *G01N 27/447* | (2006.01) |
| *G01N 27/416* | (2006.01) |
| *B82Y 15/00* | (2011.01) |
| *B82Y 5/00* | (2011.01) |
| *G01N 33/487* | (2006.01) |
| *B82Y 40/00* | (2011.01) |
| *G01N 27/327* | (2006.01) |
| *G01N 27/403* | (2006.01) |
| *G01N 33/543* | (2006.01) |

(52) U.S. Cl.
CPC ........ *G01N 33/48721* (2013.01); *B82Y 15/00* (2013.01); *B82Y 40/00* (2013.01); *G01N 27/3271* (2013.01); *G01N 27/403* (2013.01); *G01N 33/5438* (2013.01)

(58) Field of Classification Search
CPC ............ G01N 33/5438; G01N 27/403; G01N 27/3271
USPC .......... 436/149; 422/82.01; 204/451, 403.01, 204/122; 205/775
See application file for complete search history.

(56) References Cited

U.S. PATENT DOCUMENTS

| | | | |
|---|---|---|---|
| 5,578,188 A | 11/1996 | Mertens et al. | |
| 6,994,314 B2 | 2/2006 | Garnier | |
| 7,168,680 B2 | 1/2007 | Koeneman | |
| 7,238,485 B2 | 7/2007 | Akeson | |

(Continued)

FOREIGN PATENT DOCUMENTS

EP 1712891 A2 10/2006

OTHER PUBLICATIONS

Nano-Fabricated Size Exclusion Chromatograph Danielle Svehla, Sabrina Feldman, Jason Feldman, Frank Grunthaner, Partha Shakkottai, Linda del Castillo, and Victor White Jet Propulsion Techinal Report, 2002.*

(Continued)

*Primary Examiner* — Krishnan S Menon
*Assistant Examiner* — Dawn A Gerido
(74) *Attorney, Agent, or Firm* — Pillsbury Winthrop Shaw Pittman LLP

(57) ABSTRACT

Described are devices and methods for forming one or more nanomembranes including electroactive nanomembranes within a nanowell or nanotube, or combinations thereof, in a support material. Nanopores/nanochannels can be formed by the electroactive nanomembrane within corresponding nanowells. The electroactive nanomembrane is capable of controllably altering a dimension, a composition, and/or a variety of properties in response to electrical stimuli. Various embodiments also include devices/systems and methods for using the nanomembrane-containing devices for molecular separation, purification, sensing, etc.

16 Claims, 3 Drawing Sheets

400B

(56) References Cited

U.S. PATENT DOCUMENTS

| | | | |
|---|---|---|---|
| 7,250,115 | B2 | 7/2007 | Barth |
| 7,553,730 | B2 | 6/2009 | Barth |
| 7,638,024 | B2 | 12/2009 | Morita et al. |
| 7,638,034 | B2 | 12/2009 | Sansinena et al. |
| 7,923,237 | B2 | 4/2011 | Castro et al. |
| 8,968,545 | B2 | 3/2015 | Holt |
| 2002/0140414 | A1 | 10/2002 | Sohn |
| 2005/0023156 | A1 | 2/2005 | Ramsey |
| 2006/0231419 | A1 | 10/2006 | Barth |
| 2006/0275927 | A1 | 12/2006 | Dubin et al. |
| 2007/0114135 | A1 | 5/2007 | Kim et al. |
| 2007/0298511 | A1* | 12/2007 | Kang ............... G01N 33/48721 436/150 |
| 2008/0160635 | A1* | 7/2008 | Castro et al. ................. 436/501 |
| 2008/0312610 | A1 | 12/2008 | Binks |
| 2009/0167288 | A1 | 7/2009 | Reid |
| 2009/0283412 | A1* | 11/2009 | Sansinena et al. ........... 205/122 |
| 2010/0038243 | A1 | 2/2010 | White |
| 2010/0075328 | A1 | 3/2010 | Bjornson |
| 2010/0289505 | A1 | 11/2010 | Zhang |
| 2010/0310421 | A1 | 12/2010 | Oliver |
| 2010/0327255 | A1 | 12/2010 | Peng |
| 2010/0331194 | A1* | 12/2010 | Turner et al. ..................... 506/2 |
| 2011/0120890 | A1 | 5/2011 | Macpherson |
| 2011/0136676 | A1 | 6/2011 | Greene |
| 2011/0297542 | A1 | 12/2011 | Smyth |
| 2012/0034410 | A1 | 2/2012 | Baumgart |
| 2012/0097539 | A1 | 4/2012 | Qian |
| 2013/0048499 | A1 | 2/2013 | Mayer |

OTHER PUBLICATIONS

Electrooxidative Deposition of Polypyrrole and Polyaniline on Self-Assembled Monolayer Modified Electrodes Curtis N. Sayre and David M. Collard Langmuir 1997, 13, 714-722.*
Stochastic Sensing with Protein Pores Hagan Bayley, Orit Braha, and Li-Qun Gu Adv. Mater. 2000, 12, No. 2.*
Clark et al., "Continuous base identification for single-molecule nanopore DNA sequencing," Nature Nanotechnology 4, 265-270 (2009).
Ayub et al., "Precise electrochemical fabrication of sub-20 nm solid-state nanopores for single-molecule biosensing," J. Phys.: Condens. Matter 22 (2010), IPO Publishing.
Sayre et al. (1997) Electrooxidative Deposition of Polypyrrole and Polyaniline on Self-Assembled Monolayer Modified Electrodes. Langmuir, 13:714-722.
Derrington et al. (2010) Nanopore DNA sequencing with MspA. PNAS, 107 (37):16060-16065.
Malinauskas et al., 'Topical Review, Conducting polymer-based nanostructured materials: electrochemical aspects,' Nanotechnology 10P, Bristol, GB, vol. 16, No. 10, Oct. 1, 2005, R51-R62.
Sansinena et al., 'Micro-patterning of ionic reservoirs within a double bilayer lipid membrane to fabricate a 2D array of ion-channel switch based electrochemical biosensors,' 2004 NSTI Nanotechnology Conference and Trade Show, vol. 1, Jan. 1, 2004, pp. 221-223.
Peteu et al, ASC Abstract of Papers, 227th ACS National Meeting, 2004.
Cornell et al, A Biosensor that Uses Ion-Channel Switches, Nature, vol. 387, pp. 580-583, 1997.
Bayley et al., 'Stochastic Sensing with Protein Pores,' Adv. Mater. 2000, 12, No. 2, pp. 139-142.
Bayley et al., 'Resistive-Pulse Sensing-From Microbes to Molecules,' Chem. Rev. 2000,100, pp. 2575-2594.
Trojanowicz, 'Miniaturized Biochemical Sensing Devices Based on Planar Bilayer Lipid Membranes,' Fresenius J. Anal Chem (2001) 371, pp. 246-260.
Schmidt, 'Stochastic Sensors,' J. mater. Chem., 2005, 15, pp. 831-840.
Cheng et al., 'Single Ion Channel Sensitivity in Suspended Bilayers on Micromachined Supports,' Langmuir 2001, 17, 4, pp. 1240-1242.
Mara et al., 'An Asymmetric polymer Nanopore for Single Molecule Detection,' Nano Letters, 2004, vol. 4, No. 3, pp. 497-501.
Li et al., 'Ion-Beam Sculpting at Nanometere Length Scales,' Nature, vol. 412, pp. 166-169, 2001.
Saleh et al., 'An Artificial Nanopore for molecular Sensing,' Nano Letters, 2003, vol. 3, No. 1, pp. 37-38.
Bayley et al., 'Stochastic Sensors Inspired by Biology,' Nature, vol. 413, pp. 226-230, 2001.
International Search Report and Written Opinion issued on Dec. 12, 2012 in Application No. PCT/ US2012/031914.
Office Action issued on Apr. 2, 2014 in U.S. Appl. No. 13/437,839.
Office Action issued on Apr. 8, 2014 in U.S. Appl. No. 13/437,817.
Office Action issued on Nov. 22, 2013 in U.S. Appl. No. 13/437,793.
Office Action issued on Oct. 22, 2013 in U.S. Appl. No. 13/437,817.
Office Action issued on Sep. 11, 2014 in U.S. Appl. No. 13/437,839.
Shao et al., (2005) Conducting polymer polypyrrole supported bilayer lipid membranes. Biosensor and Bioelectronics, 20:1373-1379.
Xu et al., (2005) Reversible Conversion of Conducting Polymer Films from Superhydrophobic to Superhyrophilic, Angewandte Chemie International Edition, 44:6009-6012.
Office Action issued Apr. 17, 2015 in U.S. Appl. No. 13/437,817.
Office Action issued on Mar. 31, 2015 in U.S. Appl. No. 13/437,753.
Office Action issued Dec. 3, 2015 in U.S. Appl. No. 13/437,753.
Office Action issued on Sep. 6, 2015 in Chinese Application No. 201280073673.9.
Office Action issued Apr. 21, 2016 in U.S. Appl. No. 13/437,753.
Yue et al., Nanochannel and Its Application in Analytical Chemistry, 2009, Recent Advances in Biology, Biophysics, Bioengineering and Computational Chemistry, Editors: Cornelia A. Bulucea, Valerie Mladenov, Emil Pop, Monica Leba, Nikos Mastorakis, pp. 80-93.
Hiroshi, Awaji et al., Synthesis of heterosegment-junctioned hybrid nanotubes of polythiophene and herometallic nanoparticlesby sequential template-based electropolymerization, Chem. Commun., 2011. 47, pp. 6547-3549.
Notice of Allowance issued Apr. 25, 2016 in U.S. Appl. No. 13/437,817.
Stejskal, J., "Polyaniline. Preparation of a Conducting Polymer", International Union of Pure and Applied Chemistry, Pure Appl. Chem., vol. 74, No. 5, pp. 857-867, 2002, 11 pages.
Akerboom, S., et al., "Controlled Fabrication of Polypyrrole Surfaces with Overhang Structures by Colloidal Templating", Applied Materials & Interfaces, ACS Publications, 2015, 16507-16517, 11 pages.
Office Action issued on Feb. 19, 2016 in U.S. Appl. No. 14/289,445.
Office Action issued Feb. 19, 2016 in U.S. Appl. No. 14/289,388.
Office Action issued May 2, 2016 in U.S. Appl. No. 14/714,681.
Office Action issued Sep. 20, 2016 in U.S. Appl. No. 13/339,010.
Office Action issued Oct. 19, 2016 in U.S. Appl. No. 14/714,681.
Office Action issued Dec. 23, 2015 in U.S. Appl. No. 13/339,010.
Office Action issued Nov. 21, 2016 in U.S. Appl. No. 13/437,753.

* cited by examiner

100/200A-C    300B    300C    300D
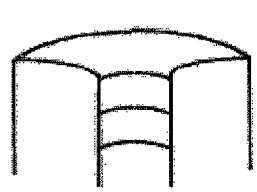
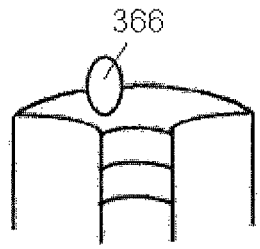
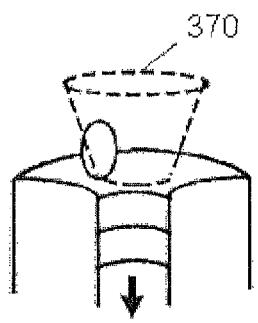
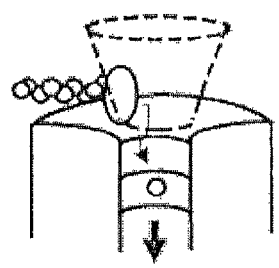
FIG. 3A   FIG. 3B   FIG. 3C   FIG. 3D
400A    400B
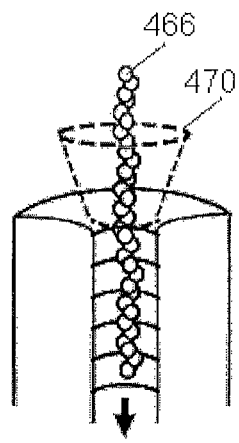
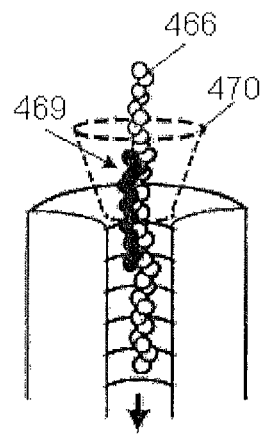
FIG. 4A   FIG. 4B

APPARATUS AND METHOD FOR MOLECULAR SEPARATION, PURIFICATION, AND SENSING

CROSS-REFERENCE TO RELATED APPLICATIONS

Reference is made to U.S. Reissue patent application Ser. No. 13/339,010, entitled "Electrochemical Detection of Single Molecules using Abiotic Nanopores having Electrically Tunable Dimensions" to Jose-Maria Sansinena et al., filed Dec. 28, 2011, which is a reissue of U.S. Pat. No. 7,638,034, issued Dec. 29, 2009, and further relates to International Patent Application No. PCT/US2012/031914, filed Apr. 2, 2012, U.S. patent application Ser. No. 13/437,817, filed Apr. 2, 2012, U.S. patent application Ser. No. 13/437,839, filed Apr. 2, 2012, U.S. patent application Ser. No. 13/437,753, filed Apr. 2, 2012, U.S. patent application Ser. No. 14/289,445, filed May 28, 2014 and U.S. patent application Ser. No. 14/289,388, filed May 28, 2014, the entire disclosures of which are incorporated herein by reference in their entireties.

FIELD OF INVENTION

The embodiments of the invention relate to an apparatus and methods for modulating the dimensionality of nanomembrane(s) and/or nanochannel(s) within nanowell(s) and/or nanotubes in a tunable fashion. The apparatus and methods can be used for a variety molecular analyte isolation and detection applications, for example to purify and/or quantify analytes such as proteins, ions, and nucleic acids. The apparatus and methods also enable other applications such as nucleic acid sequencing.

BACKGROUND

The technologies for the separation, purification, and sensing of molecules has evolved considerably over the past decades. However, these devices generally continue to require the use of expensive, fragile, complex to operate, and/or bulky instrumentation such that they cannot readily be deployed for use in the field, in doctor's offices, or at a patient's bedside. Widespread advances by nanotechnologists and the silicon manufacturing industries are particularly helping to overcome these challenges. For example, many chip-based systems are now being marketed that enable molecules like proteins, nucleic acids, ions, and small molecules to be processed, identified, and quantified.

An ongoing shortcoming, though, is that such chip-based molecular manipulation systems most often are so specialized that they can only be used for a single purpose: they can quantify DNA but they cannot be used to purify DNA; they can identify proteins; but their use cannot be extended to identify nucleic acids). In short, a robust, general-purpose nanotechnology system that can be used to separate, identify, and/or quantify molecules is currently lacking.

SUMMARY

In accordance with various embodiments, there is provided a device. The device may include one or more nanowells or nanotubes or combinations thereof disposed within a support material. Each nanotube may include one or more sidewall electrodes and/or each nanowell may include one or more sidewall electrodes and/or one or more bottom electrodes. The device may include one or more electroactive nanomembranes disposed on at least a portion of the one or more electrodes of the one or more nanowells or nanotubes or combinations thereof. The device may further include a lipid bilayer supported by or associated with the one or more electroactive nanomembranes to allow for insertion of a molecule. In embodiments, the lipid bilayer may provide for insertion and functionality testing of one or more lipophilic molecules including detergents, oils, fats, lipids, surfactants, or combinations thereof, and/or proteins including porins, ion channels, protein nanopores, membrane proteins, membrane enzymes, membrane receptors, membrane channel proteins, membrane transport proteins, complexes with and by thereof, and/or combinations thereof. Such insertion may include an insertion of just one molecule of protein.

In embodiments, the one or more electroactive nanomembranes may have a hydrophobic surface as a nucleation site or an adhesion site for promoting a rate or a stability of a lipid bilayer. Alternatively, the hydrophobic surface may be used for nucleating the formation of the lipid bilayer, and/or for adhering to stabilize the lipid bilayer. The number of lipophilic molecules or proteins or protein complexes able to be inserted in the one or more electroactive nanomembranes may be controllable or restricted by a dimension alteration of the one or more electroactive nanomembranes to decrease a surface area spanned by the lipid bilayer. In embodiments, the device may include a nanochannel or nanopore formed by the one or more electroactive nanomembranes to support or stabilize the lipid bilayer.

In accordance with various embodiments, there is provided a method for molecular separation, purification, and sensing. In such a method, one or more nanotubes or nanowells or combinations thereof are provided in a support material. Each nanotube may include one or more sidewall electrodes. Each nanowell may include one or more sidewall electrodes and/or one or more bottom electrodes. An electroactive nanomembrane may be placed on at least a portion of one electrode of the one or more nanotubes or nanowells, or combinations thereof to form a nanopore or a nanochannel within a corresponding nanotube or nanowell, wherein the electroactive nanomembrane is capable of altering a dimension, composition, hydrophobicity, hydrophilicity, charge, chemical binding, metallic, or metal binding property of the electroactive nanomembrane. An analyte may be able to move as desired in the one or more of the nanopores or nanowells, or combinations thereof.

In embodiments, one or more properties of the electroactive nanomembrane may be modulated over time such that one or more analytes are separated, partitioned, isolated, fractionated, purified, or combinations thereof according to, for example, (1) their size; (2) their wettability (e.g., hydrophobicity/hydrophilicity); (3) their charges, the electroactive nanomembrane being used as a constant barrier; (4) their chemical reactivity; (5) their being bound by one or more types of nanomembrane-attached functionalization, the functionalization including proteins, antibodies, enzymes, antibody fragments, lectins, phage, nucleic acid oligomers, nucleic acid components, aptamers, peptides, amino acids, modified amino acids, lipids, ions, small molecules, drugs, and/or combinations thereof; and/or combinations thereof, as the one or more analytes pass through the nanopore or the nanochannel formed by the electroactive nanomembrane.

In embodiments, moving the analyte may include subjecting a passive diffusion movement, an electrophoretic force, a mechanical force, or their combinations to the analyte; altering a dimension of the electroactive nanomembrane by imposing electric stimuli on the electroactive nanomembrane; and/or electrokinetically introducing a plurality of ionized molecules into the nanochannel or nanopore formed by the electroactive nanomembrane, the plurality of ionized molecules including ionized salts, nucleic acid oligomers, nucleic acid components, and combinations thereof.

In embodiments, the nanopore or the nanochannel may form one or more testing columns or wells for liquid chromatography (LC) or gas chromatography (GC). In embodiments, the movable analytes may be immobilized by neutralizing a net charge of the one or more analytes within the nanopore or the nanochannel by applying electrical stimuli as the one or more analytes move across the one or more electroactive nanomembranes. The immobilized analytes may in turn be mobilized or isolated by changing the dimension or composition of the electroactive nanomembrane; by changing a temperature or a pressure of the electroactive nanomembrane; and/or by applying a fluid to interact with the electroactive nanomembrane by electrostatic, hydrophobic, or hydrophilic interactions, and/or to disrupt target or functionalization interactions, wherein the fluid is formulated with one or more components comprising ions, ionic material, detergents, proteins, antibodies, enzymes, antibody fragments, lectins, carbohydrates, phage, ligands, nucleic acid oligomers, nucleic acid components, aptamers, peptides, amino acids, modified amino acids, lipids, small molecules, drugs, or combinations thereof.

BRIEF DESCRIPTION OF THE DRAWINGS

FIGS. 3A-3D depict analyte motion-inducing methods using devices of FIGS. 1 and/or 2A through 2C according to various embodiments of the present teachings.

FIGS. 4A-4B depict exemplary embodiments of DNA sequencing.

DETAILED DESCRIPTION

Figure 1:
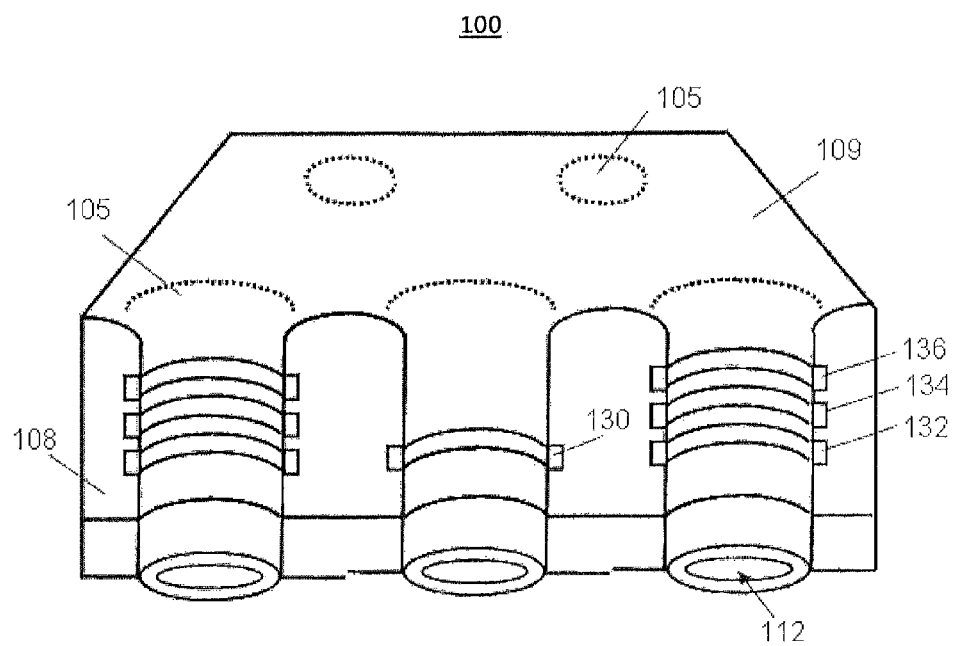
FIG. 1 is a schematic of a portion of an exemplary device including a nanowell array according to various embodiments of the present teachings.

The present disclosure describes an apparatus and methods for molecular manipulation system that is sufficiently flexible that it can be employed to separate and purify molecules as structurally and chemically diverse as proteins, nucleic acids, ions, and small molecules. The same underlying technology can be combined with sensors such as optical and electrical detectors to identify and quantify this same breadth of molecules. Further specializations of the underlying technologies open entirely new applications, too, for example including a highly scalable and robust system for sequencing DNA and RNA molecules. The key innovation enabling such a broad spectrum of capabilities relies on a novel apparatus and methods by which nanostructures, in particular nanomembranes, can be manufactured such that they can provide for tunable dimensioning. These tunable nanomembranes furthermore can be easily engineered to select for their bulk and surface properties, and/or functionalization, to enable the manipulation and quantification of a very wide range of molecule types.

As used in the specification and claims, the singular forms "a", "an" and "the" include plural references unless the context clearly dictates otherwise. In embodiments, terms such as "an array" or "the nanowell" may include a plurality of arrays or nanowells, respectively, unless the context clearly dictates otherwise.

In embodiments, the terms "up" and "down" connote only that they represent a general directional flow of a given material and that, when used in the same context, represent generally opposing flow directionalities.

In embodiments, the term "bulk," as in the "bulk" of a nanomembrane or a nanomembrane's "bulk" properties, do not necessarily connote any absolute proportionality as to how much of the entirety of a given property is due to the "bulk" versus the remainder that differs from the "bulk." As a non-limiting example, a thin film of one nanomembrane material can be layered over the bulk of another membrane material such that the thin film occupies 5-10% of the nanomembrane's total volume. This thin film may be induced to occupy 40-50% of the same nanomembrane's total volume when it is subjected to given electroactivity-inducing imposed electrical stimuli. Thus, "bulk" versus not "bulk" is necessarily contextual in the provided embodiments.

"Solid support," "support," and "support material" are referred to herein as a material or group of materials having a rigid or semi-rigid surface or surfaces. In some aspects, at least one surface of the solid support will be substantially flat, although in some aspects it may be desirable to make use of solid supports bearing, for example, raised regions, pins, etched trenches, and/or the like. A variety of materials can be used for the solid support including, but without limitation, silicon/silicon derivatives, polymers, ceramics, glass, metals, and/or other possible materials. Multiple materials may be used to manufacture a given solid support.

A solid support may be manipulated such that the mode(s) by which it supports a given structure or structures can be altered during the course of its manufacture and use. In embodiments, the solid support may be subjected to manipulations such as chemical or plasma etching to change the three-dimensional manner in which it supports these structures. The solid support also may be derivatized to change the composition of the material in which the support of the structures is provided. In embodiments, a solid support can be derivatized with one or more molecules known to modify its surface properties to make it more hydrophobic, hydrophilic, ion impermeable, chemically reactive, and/or electrically insulating. Multiple cycles of solid support derivatization with the same or different molecules also can be employed. The solid support also can be coated with one or more materials. Such surface coatings also can allow a desired solid support in embodiments to make it more hydrophobic, hydrophilic, ion impermeable, chemically reactive, and/or electrically insulating. These coatings can be added or removed repeatedly during the manufacture and use of a given solid support.

A "chamber" is a space that occurs over the surface of a solid support. This space may be defined by some type of package or cell that effectively forms an enclosure over a solid support's surface. A chamber may be formed with essentially any dimensionality, and may also include one or more inlets and outlets for example to allow for fluids and/or gases to be passed over the solid support's surface. More than one chamber may be placed over the solid support's surface, too. Chambers may be manufactured such that they can be readily placed or removed, materials can be transferred or not between them, etc. These chamber configurations also can be modified any number of times over the course of a given application. Chambers can be formed of any material that is compatible with a given application, for example including, but without limitation, silicon/silicon derivatives, polymers, plastics, rubber, ceramics, glass, metals, and/or other possible materials. Chamber materials also can be changed over the course of the manufacture and use of a given solid support, for example, but without limitation, making use of the same or different derivatizations and coatings used to modify a solid support.

An "array" is an intentionally created collection of two or more structural elements on, and/or in, a solid support. Arrays are manufactured by wide variety of means, for example making use of the diverse methods of the semiconductor manufacturing industry. Thus, arrays could take a wide variety of forms, for example bearing two or more electrodes, nanowells, nanotubes, and/or trenches, and so forth. An array could either be a macroarray or a microarray, depending on the size of the structural elements on the solid support. A macroarray generally contains structural element sizes of about 300 microns or larger. A microarray would generally contain structural element sizes of less than 300 microns. However, it should be noted that macroarrays and microarrays share essentially similar properties, differing in the art for example regarding their dimensional scales, how they are manufactured, and/or how materials are deposited upon them. Thus, the term "array" is used herein to describe both macroarrays and microarrays for the invention herein, and it should be understood that this term is not intended to actually denote any dimensionality specifications or limitations. The total surface area of an array can significantly exceed the scale of the structural elements on its surface; microarrays for example may occupy multiple square centimeters of a solid support and macroarrays may occupy less than a square centimeter of solid support.

"Functionalized arrays" are arrays that have been further modified with molecules. These molecules may be prepared synthetically, biosynthetically, and/or purified, and then attached to an array to functionalize it. Functionalization may also be done "in situ" such that molecules are synthesized, purified, etc in place on an array's surface, for example, but not limited to, making use at least initially of one or more of the electrochemical reactions described herein. The molecules used to functionalize an array can be identical or different from each other on a given array. Furthermore, functionalized arrays can assume a variety of formats, in embodiments, bearing polymers, libraries of soluble molecules; and/or libraries of molecules tethered to polymers. The molecule libraries used for functionalization can include, but are not limited to, proteins, enzymes, antibodies, antibody fragments, phage, nucleic acids (DNAs, RNAs), aptamers, peptides, ions, small molecules, drugs, and/or combinations thereof. Exemplary enzymes can include kinases, phosphatases, nucleases (DNA and RNA cleaving), synthases (e.g., DNA polymerases), oxidases (e.g., glucose oxidases), peroxidases, reductases, and/or their combinations. Suitable chemistries for the functionalization can include the use of cross-linkers, heterobifunctional cross-linkers, and/or light-activated cross-linkers. Other chemistries, such as electrochemical coupling reactions through one or more corresponding electrodes, can also be used.

A "well" or a "nanowell" is a three-dimensional structural element that is manufactured to form a depression into a solid support. The overall dimensions of a well or nanowell can be varied tremendously depending upon the manufacturing methods and the nature of the solid support used. A "well" describes this structural element with its smallest dimension (e.g., diameter, depth) larger than about 300 microns. A "nanowell" describes this structural element with its smallest dimension smaller than about 300 microns. However, it should be noted that wells and nanowells share essentially similar properties, differing in the art for example regarding their dimensional scales, how they are manufactured, and/or how materials are deposited upon them. Thus, the term "nanowell" is used to describe both wells and nanowells for the invention herein, and it should be understood that this term is not intended to actually denote any dimensionality specifications or limitations. Similarly, an array of two or more actual nanowells and/or wells is summarized by reference herein as being an array of nanowells even though it should be understood that both wells and nanowells can be manufactured in the same solid support. Although the nanowells shown in figures herein have an essentially circular cross section, this dimensionality is actually used for illustrative purpose. One of ordinary skill in the art will appreciate that any other, regular or irregular, dimensionalities of nanowells are contemplated to accommodate various embodiments of the present teachings. In fact, nanowells can have essentially any dimensionality or (a) symmetry, and may be limited, for example, only by the capabilities of the manufacturing method used to form a given solid support, or the application for which it is being made. Thus, nanowells can have a dimensionality in their cross-sections including, but not limited to, circular, square, rectangle, polygon, or any other suitable cross-section dimensionalities, and they also can have essentially no discernable shape in their cross-sections. A nanowell can have straight sidewall. Alternatively, a nanowell can have non-straight sidewalk, for example, having one or more overhangs, indentations, lips, steps, cupping, bulges, angles, etc., and these features can differ anywhere along the sidewall of the nanowell. A given solid support can be manufactured to have one nanowell, or to have one or more arrays of nanowells, and these multiple nanowells can have the same or different dimensionalities and (a) symmetries.

As defined herein, a cross-section of a nanowell relates to a two-dimensional representational view of a given example of this structure that largely bisects across its sidewall. A lateral-section of a nanowell relates to a two dimensional representational view of a given example of this structure that that largely runs in parallel with its sidewalls. For a nanowell with varying/irregular sidewall profiles, however, cross-section(s) and lateral section(s) representations may significantly overlap.

Various configurations of nanowells in an array can be used. In embodiments, a nanowell array can be configured periodically or non-periodically. The nanowells in an array can be aligned in square, hexagonal, or any other pattern, or can lack any alignment or pattern. Nanowell arrays also can have nanowells placed in one or more patterns on one portion of their surfaces, while other portions have nanowells placed in no particular pattern.

"Tubes" and "nanotubes" are depressions formed in a solid support such that they effectively lack a bottom, or at least that they lack a bottom that is directly attached to the sidewall as with a nanowell. Thus, a tube or nanotube entirely pierces a given solid support. The overall dimensions of tubes and nanotubes can be varied tremendously depending upon the manufacturing methods and the nature of the solid support used. A "tube" describes this structural element with its smallest dimension larger than about 300 microns, A "nanotube" is a structural element with its smallest dimension smaller than about 300 microns. However, it should be noted that tubes and nanotubes share essentially similar properties, differing in the art for example regarding their dimensional scales, how they are manufactured, and/or how materials are deposited upon them. Thus, the term "nanotube" is used to describe both tubes and nanotubes for the invention herein, and it should be understood that this term is not intended to actually denote any dimensionality specifications or limitations. Similarly, an array of two or more actual nanotubes and/or tubes is summarized by reference herein as being an array of nanotubes even though it should be understood that both tubes and nanotubes can be manufactured in the same solid support.

As used herein, a cross-section of a nanotube relates to a two-dimensional representational view of a given example of this structure that largely bisects across its sidewall. A lateral-section of a nanotube relates to a two dimensional representational view of a given example of this structure that largely runs in parallel with its sidewalls. For a nanowell with varying/irregular sidewall profiles, however, cross-section(s) and lateral section(s) representations may significantly overlap.

Nanotubes may be formed essentially in any dimensionality and, as with nanowells, and their "depth" is only limited by the thickness of the solid support in which they are formed. Although the nanotubes shown in figures herein have a circular cross section, this dimensionality is actually used for illustrative purpose. One of ordinary skill in the art will know that any other, regular or irregular, dimensionalities of nanotubes are contemplated to accommodate various embodiments of the present teachings, as with nanowells. When more than one nanotube is formed in a solid support, the resulting structure becomes a nanotube array. The number of nanotubes formed, their arrangement with respect to each other, and that each may be identical or in any combination(s) of distinctiveness with respect to each other is possible in embodiments. One or more nanotubes may form a connection between a single chamber, between two distinct chambers, between any number of distinct chambers, and/or between any combinations of connected or disconnected chambers.

Nanotubes also can be made to form a connection between two other nanotubes in a given solid support. The dimensionalities of such "connecting nanotubes" formed between two or more nanotubes within a solid support can be as varied as that of the nanotubes themselves. Thus, since connecting nanotubes can have essentially the same properties as nanotubes, connecting nanotubes also are referred to herein as "nanotubes."

It is well known in the manufacturing industry that two surfaces can be combined together in a precise joined orientation and then appropriately fixed together for example with clamps, glues, solder, and the like. In this manner, three-dimensional structural elements can be formed by the combination of two or more solid support as the surfaces are brought together. Thus, these methods can be used for example to form nanotubes and/or nanowells, as well as arrays thereof, which result from the combination of two or more solid supports.

A "nanochannel" is defined herein as the open space or void within a solid support that is bounded by a given nanotube's sidewall and sidewall electrodes, as well as the void within a solid support that is bounded by a given nanowell's sidewall and bottom, and sidewall and bottom electrodes. As such, the dimensionalities of a given nanochannel can be as varied as the wide range of dimensionalities of the possible nanotubes and/or nanowell structures described herein. Similarly, the two or more nanochannels in a given solid support can have the same and/or markedly different dimensionalities just as the nanotube(s) and/or nanowell(s) bounding the nanochannels can have the same and/or markedly different dimensionalities in that solid support. Nanochannels also can be formed by the combination of two or more solid supports just as nanotubes and/or nanowells can be formed in the same manner.

As defined herein, a cross-section of a nanochannel relates to a two-dimensional representational view of a given example of this structure which largely bisects across its outer perimeter as provided by a given combination of dimensionalities of a nanowell's or nanotube's sidewall, sidewall electrodes, bottom, and nanomembranes. A lateral-section of a nanochannel relates to a two dimensional representational view of a given example of this structure which largely runs in parallel with its outer perimeter. For a nanochannel with varying/irregular perimeter profiles, however, cross-section(s) and lateral section(s) representations may significantly overlap.

As used herein, an "electrode" is an electrically active surface that can be made of any suitable conductive material or materials. When more than one electrode is placed on a solid support, as in an array, these can be the same or different conductive materials. The conductive electrode material can for example, but is not limited to, metals, conductive polymers, carbon-based conductive structures, conductive composites, and/or combinations thereof. Exemplary metals can include silver, gold, platinum, copper, titanium, aluminum, tungsten, and/or their combinations. Exemplary conductive polymers can be polyacetylene, polyphenylene vinylene, polypyrrole, polythiophene, polyaniline, polyphenylene sulfide, and/or their combinations. Exemplary carbon-based conductive structures can include carbon films, plates, tubes, rods, buckyballs, graphene, and/or their combinations. Exemplary conductive composites include electrically conductive metal matrixes, epoxies, adhesives, silicones, laminates, elastomers, carbonized plastics, and/or their combinations.

Optionally, electrodes can be made of one or more materials that are further useful in providing for additional functionalities beyond electrical conductivity. In embodiments, metals can be used to form an electrode which can undergo a chemical reaction in the presence of an appropriate molecule such that they are become oxidized or reduced. Such an oxidation or reduction can result in the electrode becoming positively or negatively charged, a result that can be monitored by a wide range of methods known in the art. Silver metal undergoes the silver/silver chloride reaction in the presence of chloride ions is one example of many known in the art for how such a functionality can be made available for nanotube and nanowell electrodes.

Electrodes also can be subjected to one or more derivatizations to impart other functionalities in addition to conductivity. In embodiments, metals such as silver and platinum can be reacted with oxygen to form an oxide. Such a metal oxide may be further reacted, for example, with the deposited nanomembrane material described herein such that the two materials become covalently bonded together. Thus, by choosing which electrodes are derivatized or not, this can serve as a method for selecting which electrode becomes a deposition site or not.

Electrodes also can be coated with one or more materials to provide for functionality in addition to conductivity. In embodiments, an electrode can be coated with materials to provide for chemical reaction resistance, electrical passivation, a hydrophilic or hydrophobic surface, a neutrally charged surface, a positively or negatively charged surface, etc. Such electrode coatings also can allow a desired electrode or a group of electrodes to be used as reaction site for electrochemical synthesis and/or for inhibiting corresponding electrode(s) from participating and/or being affected by any possible chemical reactions in embodiments.

It should be noted, though, that a wide range of other additional functionalities, derivatization methods, and coating methods are well known in the art for the conductive electrode materials described herein, and these also can be used to impart a similarly wide range of capabilities beyond the examples described. Such functionalities, derivatives, and coatings can be deposited and removed repeatedly during manufacturing and use of the apparatus provided herein.

Each nanowell and/or nanotube can include one or more electrodes configured along its sidewall, which are referred herein as "sidewall electrode(s)." Furthermore, a nanowell may have one or more electrodes configured at the bottom of the nanowell, which are referred herein as "bottom electrode(s)." In embodiments, one or more "bias electrodes" also can be included. A bias electrode is an electrode that is located elsewhere other than the sidewall or bottom of the one or more nanowells and/or nanotubes in a solid support. Thus, a bias electrode or bias electrodes may be placed on the solid support's surface(s) (i.e., on areas of a given solid support that is not part of a nanotube or nanowell), and/or placed in the one or more chamber onto which the solid support is attached or mounted. Note that in the range of possible dimensionalities of nanotubes and nanowells that it can be ambiguous as to whether a given electrode is a sidewall, bottom, or bias electrode. It also can be useful to manufacture electrodes that cross multiple surfaces of nanotube or nanowell (e.g., spanning across the bottom, sidewall, and out onto the surface of a nanowell). Nonetheless, these types of electrodes can have the same general dimensional and electronic properties as the more obviously defined sidewall, bottom, and bias electrodes. Therefore, these types of electrodes are referred to herein as sidewall electrodes, even though their particular location(s) may not be clearly limited to the confines of a given sidewall.

Sidewall electrodes can be configured in any dimensionality, so long as they remain at least partially placed on the sidewall of a given nanowell or nanotube. For example, sidewall electrodes can be manufactured such that they partially to completely encircle/ring a nanotube or nanowell's sidewall. Sidewall electrodes also can be crafted to have essentially any dimensionality, for example being rectangular, circular, banded, asymmetric, etc, and each can be independently operable electronically. Sidewall electrodes also can be formed by breaking an electronically connected electrode into two or more segments along the sidewall, wherein the broken segments can have same or different dimensionalities that are separated by electrically resistive materials. Such electrically resistive material can be, but is not limited to, silicon dioxide, silicon nitride, polyimide(s), photoresist materials, and combinations thereof. Any distance can separate sidewall electrodes from one another so long as they remain associated within the confines of a given sidewall. These segmented electrodes may be connected to the same or independent electronics elements (in embodiments, capacitors, voltage sources, current sources, resistors, amplifiers, analog-to-digital converters, sensors, etc). Sidewall electrodes also can be placed in any configuration such that they occur as stacks of electrodes separated by electrically insulating material(s). Theses stacked electrodes, too, may be connected to the same or independent electronics elements. The types of sidewall electrodes employed in a nanotube or nanowell array may be the same or different, being limited only by the mode of manufacturing used to form them, the application for which they are intended, and the type of electrical controls used to operate them.

Bottom electrodes of a nanowell have a similar flexibility in dimensionality as that of the sidewall electrodes so long as they remain at least partially associated in the confines of the bottom of a nanowell. Bottom electrodes may be any dimensionality, for example being square, circular, ringed, asymmetric, etc. In the instances in which more than one bottom electrode is placed in a nanowell, these also can be placed to be in no particular pattern with respect to each other, and/or they may be patterned such as in a grid, as concentric elements, etc. When one or more bottom electrodes are utilized, these can be separated from each other by some electrically insulating material such as, but not limited to, silicon dioxide, silicon nitride, polyimide(s), photoresist materials, and combinations thereof. Bottom electrodes can be separated from one another by any distance so long as they remain associated within confines of a given well's or nanowell's bottom. Bottom electrodes, too, may be connected to the same or independently operating electrical elements.

Bias electrodes have the same flexibility in their dimensionalities and placement with respect to each other as is provided for the other electrode types described herein.

The sidewall, bottom, and bias electrodes in the one or more nanotubes and/or nanowells in a solid support need not be made to be flush with the solid support surface. In embodiments, these electrodes can be manufactured such that they are placed in depressions within and/or extensions above the local surface of the solid support or chamber. Similarly, these electrodes themselves can form a depression within and/or extension above the local surface of the solid support or chamber. These electrodes also can be manufactured such that they generally follow the plane of the local solid support surface at one place and yet are within depressions below and/or extensions above the local solid support in another place(s). Similarly, the electrode material itself can be fashioned to further define the topology of a local surface, for example by being manufactured to have a depression(s) and/or extension(s) that may or may not reflect the contours of the local solid support surface.

In the case of nanotubes, one or more secondary and/or bias electrodes can be employed to serve as the pseudo-bottom electrode(s). Pseudo-bottom electrodes can be the sidewall and/or bottom electrode(s) in the nanowell(s) facing away from the 'top' chamber of a nanotube. They also can be the bias electrode(s) on the surfaces of either or, both sides of a solid support containing a nanotube, and/or in the chamber(s) attached to either or both sides the solid support. Pseudo-bias electrodes have the same flexibility in their dimensionalities and placement with respect to each other as is provided for the other electrode types described herein.

During operation, the sidewall electrodes and/or/or the bottom electrodes and/or the bias electrodes each can be operated independently, in series, and/or in parallel to accommodate a given requirement. These operational modes furthermore can be changed over time as required. Additional circuitry providing for all electronic operations as known in the art also may be incorporated in the solid support and connected to the electrodes. In embodiments, the electrodes can be connected to electrical components found in the art including, but not limited to, components that provide electrical connectivity by any appropriate mode known in the art; control and delivery of voltage, current, and/or resistance, including from being invariant to enabling any desired variation in amplitude, frequency, and/or wave form by any appropriate mode known in the art; signal sensing, amplification, noise reduction, smoothing, analog-to-digital conversion, and/or any other signal processing by any appropriate mode known in the art; data communication in analog or digital formats by any appropriate mode known in the art; data storage in analog or digital formats by any appropriate mode known in the art; and/or any combinations of the above.

In instances in which two solid surfaces are combined together to form nanotubes and/or nanowells, it is well known in the industry that electrical circuitry can be connected across the resulting junction of the two solid supports if this is desired. In the semiconductor industry, for example, one mode for making such electrical connections is to employ a technique called making a "flip-chip" or a "controlled collapse chip connection.". In this manner, three-dimensional electrical elements can be formed as the surfaces are brought together. Thus, such methods can be used for example to form one or more electrodes that connect across tubes, nanotubes, wells, and nanowells that are formed by the combination of more than one solid supports. Such electrical elements like electrodes can have all of the same dependent and/or independent functionalities of the bottom, sidewall, and bias electrode(s) described for nanowells and/or nanotubes in a single solid support. It should be noted that the particular mode by which flip-chips are generally formed in the silicon industry does not limit the means by which the apparatus described herein can be manufactured. Two or more solid supports also can be brought together in an acceptably stable and functional complex via the use of glues, thermal fusion, etc., as is appropriate for a given application. It may be desirable to bring two or more solid support surfaces for reasons other than forming new electrical connections, though. For example, surfaces may be brought together simply to form other topologies that make no further modification(s) to their pre-existing electrode configurations. In any case, whether, as defined herein to indicate the formation of new structures by bringing together one or more solid support for whatever reason and/or by whatever method, the resulting apparatus is referred to herein as being a "flip-chip."

As used herein, the term "membrane" or "nanomembrane" refers to an electroactive material or layer of materials that is deposited on one or more electrodes. As used herein, the electrode upon which a membrane or nanomembrane is deposited is a "primary electrode." Primary electrodes can be one or more sidewall, bottom, or bias electrode, or any combinations of these electrodes. These primary electrodes can be electronically interconnected and/or independently operable. A "membrane" generally refers to a layer of electroactive material that is deposited over the larger sized electrode structures that generally are associated with tubes and wells, while a "nanomembrane" is deposited over smaller sized electrode structures such as those generally associated with nanotubes and nanowells. However, it is understood that the properties of membranes and nanomembranes essentially can be the same except for how these differ due to their lesser or greater thickness, distances covered, etc. Thus, the term "nanomembrane" is used to describe both membranes and nanomembranes herein, and it should be understood that this term is not intended to actually denote any dimensionality specifications or limitations. Similarly, in the instance in which a nanotube and/or nanowell array bearing two or more actual nanomembranes and/or membranes, such a system is summarized by reference herein as being an array bearing nanomembranes even though it should be understood that both scales of these structures can be manufactured in the same solid support.

It can be desirable to deposit an "electroactive nanomembrane" on a sidewall primary electrode that encircles the interior of a nanotube and/or a nanowell. These encircling primary sidewall electrodes can be manufactured either directly in the a sidewalls of a nanotube and/or nanowell, or they can be formed as two or more solid supports containing portions of these structures are brought together as per the "flip-chip" methodologies as described herein. In either case, the resulting deposited nanomembrane on such encircling electrodes can form ring of deposited material that also encircles the interior of a nanotube and/or a nanowell. As defined herein, this apparatus and methodology results in the formation of an "encircling nanomembrane." Illustrations provided herein of encircling nanomembranes are depicted as being an annulus (i.e., being essentially circular or donut-shaped in its profile). However, encircling membranes in fact can be deposited in any shape. For example, when deposited on cylindrically shaped surfaces, a thinly deposited encircling nanomembrane will generally conform to this cylindrical shape. A more thickly deposited encircling nanomembrane nonetheless can assume any shape that may or may not be essentially circular. Note that one or more encircling nanomembranes can be deposited on the interior of a given nanotube or nanowell, as more than one encircling electrode can be placed with the solid supports of these structures.

As used herein, unless otherwise specified, the term "nanomembrane" generally refers to "electroactive nanomembrane" in this disclosure, although one or more non-electroactive nanomembrane(s) can be used in combination with the electroactive nanomembrane(s). In embodiments, electroactive nanomembrane(s) can be formed over nanomembrane(s) that are electroactive and/or non-electroactive on corresponding electrode(s) as disclosed herein. In embodiments, non-electroactive nanomembrane(s) also can be formed over nanomembrane(s) that are electroactive and/or non-electroactive on corresponding electrode(s) as disclosed herein.

In any case, the presence of a given encircling nanomembrane contributes to the dimensionality of the nanochannel as described herein, and this contribution can change in response to the given nanomembrane's electroactivity in response to applied electrical stimuli.

Illustrations of the interior cross-section of an encircling nanomembrane are depicted herein as defining a space that is essentially circular. However, the interior cross section of the nanochannel that is surrounded by an encircling nanomembrane can be essentially any shape. Thus, regardless of its interior cross-section shape, the nanochannel that is surrounded by an encircling nanomembrane is defined herein as being a "nanopore," A nanopore can be of any dimension along its cross-section and lateral-section so long as it remains surrounded by an encircling nanomembrane. In addition, while it can be desirable for a nanopore to be manufactured such that it essentially is centrally placed in a nanowell or nanotube, this is not a requirement (in embodiments, one or more nanopores can be placed anywhere in an encircling nanomembrane). Note that one or more nanopores can be formed in an encircling nanomembrane with a relatively thin lateral-section. In such instances, the lateral-section of such a nanopore is comparatively small (in embodiments, but not limited to, tens to hundreds of nanometers in lateral-section). Similarly, one or more nanopores can be formed in encircling nanomembranes of very long lateral-section in embodiments, but not limited to, forming one or more nanopores in an encircling nanomembrane spanning more than a millimeter in its lateral-section). A given nanopore's lateral-section and cross-section also may vary along the length of the nanochannel that forms it, so long as it remains entirely encircled by nanomembrane.

The term "electroactive" refers to a property of a material that exhibits electrical activity or response to electrical stimuli. The deposited nanomembrane material or layer of materials described herein can be electroactive (i.e., having "electroactivity") in that it undergoes a dimensionality change in response to imposed electrical stimuli such as electrical current, voltage, or electrical waveform provided at the one or more primary electrodes upon which it is deposited. However, the deposited nanomembrane material or layer of materials could be non-electroactive nanomembranes in the system. Note that nanomembrane electroactivity also can be elicited by imposing electrical stimuli at one or more electrodes other than the primary electrode, herein described as "secondary electrodes." Such secondary electrodes can be one or more sidewall, bottom, and/or bias electrodes. Furthermore, the electrical stimuli can be provided by combinations of primary and/or secondary electrodes.

As used herein, a "dimensionality change" describes any modification of a nanomembrane's three-dimensional conformation resulting from imposed electrical stimuli at one or more primary or secondary electrodes. A dimensionality change can include, but is not limited to, an increase and/or a decrease in a nanomembrane's length, thickness, breadth, bending, twisting, looping, etc. Such dimensionality changes may or may not be accompanied by a change in a nanomembrane's density. Such dimensionality changes also may or may not be accompanied by a change in the nanomembrane's molecular composition, and/or or chemical bond structure. A nanomembrane's dimensionality change may or may not include the addition or removal of non-covalently bound or covalently bound material from its surface, or within its internal structure. Thus, for example, a dimensional change may occur via the polymerization or depolymerization of just one molecule at the surface of a pre-existing nanomembrane's surface or within its interior. Therefore, in embodiments, the scale of a nanomembrane's dimensional change as described herein can proceed via the formation or breaking of a single chemical bond, and/or via a compositional change as small as the inclusion or removal of a single molecule in non-covalent and/or covalent association with a given nanomembrane.

As used herein, making use of a nanomembrane's "electroactivity" entails employing instrumentation and methods to control the imposition of electrical stimuli such as, but not limited to, a voltage or current in a given electrical waveform to an electrode of interest in order to induce a nanomembrane's dimensional change. There are a wide variety of voltage, current, and electrical waveform control apparatus and methods well known in the art to provide for this use. These include, but are not limited to, apparatus and methods providing for the generation of: a direct current; an alternating current; a current or voltage modulated as a sine, square, saw-tooth, etc. waveform; a cyclic voltammetry-driven current or voltage; an electric waveform supplied at constant voltage, constant current, or constant power; voltages and/or currents varying in any type of amplitude and/or frequency; voltages a; and/or currents varying in their duration and/or number of pulses; and combinations thereof. While it is understood that the instrumentation and methods to enable controls for imposing a wide variety of apparatus and methods for imposing voltages, currents, and/or electrical waveforms at an electrode are known in the art, the breadth of these available options are summarized by reference herein as imposing "electrical stimuli" at an electrode.

Thus, in the instance in which one or more nanomembranes is deposited on a sidewall and/or bottom of a nanowell, and/or the sidewall of a nanotube, an electroactive nanomembrane's, or nanomembranes', contribution to the dimensionality of the nanochannel(s) can change as it is subjected to the imposition of electrical stimuli.

Nanomembranes can be deposited by a wide range of manufacturing procedures. Non-electrochemical methods include, but are not limited to, methods such as spraying, vapor-phase deposition, sputtering, spin coating, precipitation, in situ polymerization by means such as heat- and/or photo-curing, multilayer deposition with the well layer being a sacrificial material that is etched away to create a material membrane over a well, etc.

Such a deposited membrane can be in close, but non-covalently attached proximity, to the given primary electrode, or it can be directly attached to the given primary electrode such as via covalent chemical bonding. The latter instance generally requires the electrode to be composed of a material that can undergo chemical bonding, or it has been derivatized and/or coated with a material that enables chemical bond formation to occur.

Examples of electroactive nanomembrane materials that can be deposited on primary electrodes include, but are not limited to, dielectric electroactive polymers in embodiments (e.g., certain types of silicone and acrylic elastomers), ferroelectric electroactive polymers in embodiments (e.g., polyvinylidene fluoride polymers), ionic electroactive polymers in embodiments (e.g., certain conductive polymers, ionic polymer-metal composites, and responsive gels), and/or their combinations.

Some deposited electroactive nanomembrane materials can be induced to change dimensionality even during their deposition in response to the imposition of electrical stimuli at the primary electrode(s) upon which they are being deposited. Some electroactive nanomembrane materials also can be induced to change dimensionality during their formation via electrical stimuli being imposed at the secondary electrode(s) in the solid support and/or the chamber(s).

Nanomembranes also can be electroactive in that these membranes are deposited in an electrically tunable dimensionality at the primary electrode(s) by imposing electrical stimuli that induces chemical bond formation of monomers into polymers via direct and/or indirect electrochemical reactions. Thus, such electroactive nanomembranes are deposited by electrochemical means. Electrochemical reactions of certain monomers to form such electrically conductive polymers such as nanomembranes are well known in the art (see Malinauskas et al., Nanotechnology, 2005). Thus, as sufficient electrical stimuli are imposed to the desired primary electrode(s), certain electroactive monomer molecules in a solution contacting that electrode can be induced to undergo chemical bond formation that results in a nanomembrane deposition. The resulting nanomembrane either can be in close, but non-covalently bonded, proximity to one or more primary electrodes, or it can be covalently attached to one or more primary electrodes. As described herein, an electrochemically deposited nanomembrane is at least initially electrically conductive such that imposed electrical stimuli at the primary electrode(s) upon which the nanomembrane is being deposited can propagate through the nanomembrane itself. Therefore, imposed electrical stimuli at a primary electrode can transfer through the electrically conductive nanomembrane such that additional monomer at least initially is incorporated into the nanomembrane elsewhere along its surface, and/or polymer is removed from its surface. For this reason, the dimensionality of the electrochemical reaction to form such nanomembranes thereby is electrically tunable in its dimensionality based upon whether or not electrical stimuli are applied at the primary electrode(s).

The one or more monomers chosen for example in a later stage of electrochemically-induced deposition also can be selected for properties such that the resulting polymer material has diminished to entirely looses electrical conductivity. Such types of monomers, therefore, can be chosen to effectively terminate an electrochemical deposition reaction at a given primary electrode(s). Such a process can be useful to diminish or eliminate the dimensional tenability of one or more electroactive nanomembranes, while preserving electrical tenability at other electroactive nanomembranes.

Some electrochemically deposited nanomembranes also can be chosen to be composed of materials that can be induced to change dimensionality during a desired deposition reaction that also responds to an imposition of electrical stimuli at the secondary electrode(s). In such instances, one or more secondary electrode can be energized with electrical stimuli that are too low to provide for polymer formation (i.e., so that they do not themselves become primary electrodes upon which polymer nanomembrane formation occurs), but with sufficient electrical stimuli to contribute to the dimensionality/conformation of the nanomembrane being formed on a primary electrode(s). Similarly, the secondary electrodes also can be derivatized or coated such that they themselves are not subjected to an electrochemical deposition processes despite being subjected to imposed electrical stimuli that otherwise could induce nanomembrane formation.

Note that some deposited electroactive membranes, whether deposited by electrochemical or non-electrochemical means, also can be depolymerized or have their deposited material removed by both non-electrochemical and/or electrochemical means. For example, nanomembranes can be deposited using energetic neutral atom beam lithography/epitaxy as described in U.S. Pat. No. 7,638,034.

Non-electrochemical and/or electrochemically deposited nanomembranes can be chosen to be composed of materials with rigidity such that they maintain a desired dimensionality only while one or more dimensionality-modulating electrodes are no longer exerting their imposed electrical stimuli-driven force effects on the polymer. Furthermore, nanomembranes also can be composed of materials with rigidity such that its dimensionality modulation is maintained, or even further modulated after its manufacture while under imposed electrical stimuli-driven force effects.

Electrically tunable nanomembranes, whether deposited electrochemically or non-electrochemically by other means, can be deposited virtually in any dimensionality. The embodiments of their dimensionalities are limited only by matters such as the availability of manufacturing methods, the stability of the nanomembrane post-manufacturing, scalability, achieving the properties required for a given application, etc.

In the instances in which a given deposition method results in a molecular monolayer or similarly thin nanomembrane at the primary electrode(s), the deposited nanomembrane's dimensionality generally conforms to the dimensionality of the primary electrode(s) itself. However, it also can be desirable to employ deposition methods to form a given nanomembrane that project significantly into a nanowell's or nanotube's interior. More deeply deposited nanomembranes can be in a very wide variety of forms including, but not limited to, forming structures such as rods, loops, wedges, fans, layers, tubes, cones, interwoven lines, sheets, etc.

Electrochemical and other deposition methods can provide for nanomembranes that join two or more electrodes. In the instances in which the deposited material is electrically conductive, the resulting nanomembrane connecting two or more electrodes can function essentially as an electrical connection between these electrodes.

In the instance of an electrochemical polymerization method being used to drive nanomembrane deposition, a sidewall primary electrode can be employed as the initial site of polymer deposition and then one or more secondary electrodes can be appropriately energized to attract the growing polymer towards their surface. Such a reaction can be stopped at any dimensionality as the nanomembrane extends from the primary electrode towards one or more secondary electrodes. The deposition also can be continued until the membrane contacts and forms an electrically conducting bridge between the primary and the secondary electrode(s). The secondary electrode(s) used to guide the growth of the electroactive polymer functionally in this instance becomes a primary electrode(s) once the nanomembrane becomes deposited on it.

An indirect, or coupled, electrochemical reaction also can be used to manufacture nanomembranes on a primary electrode. In embodiments, indirect electrochemistries can include a 1,4-benzoquinone reaction (see Formula I) provided by way of an example of the range of coupled electrochemical reactions that can be employed to generate conditions useful for synthetic membrane formation. In this instance, electrochemistry can be used to react with 1,4-benzoquinone to produce ionized hydrogen protons (i.e., creating a solution containing $H^+$, thereby creating an acidic solution). The resulting protons in the solution also can drive subsequent chemical reactions for nanomembrane formation in the instances in which monomers, ions, and/or doping agents have been chosen which can be caused to form nanomembranes due to the formation of a localized acidic solution. It is understood that other indirect electrochemical reactions similarly could be used to cause the formation of nanomembranes, that these electrochemistries can be driven by primary and/or secondary electrodes, that they can involve the use of coatings and/or derivatization at either or both electrodes to keep the nanomembrane formation localized, and so forth.

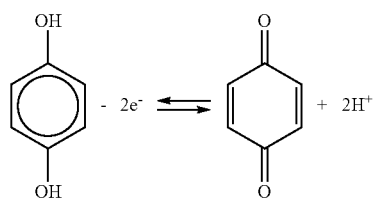

Formula 1

Nanomembranes can have specific mechanical or durability properties. In embodiments, they may be manufactured to be mechanically resistant or prone to a dimensionality change when being moved for example from aqueous to dry environments, being moved between aqueous solutions of different ionic strength or pH, being moved between aqueous to organic solvents, being subjected to shipping and/or prolonged storage, etc.

Electrochemically deposited nanomembranes can include one or more polymers, metal materials, and/or other suitable materials that can be formed from the precursor materials by electrochemistries on electrodes. These different polymers and/or materials can be made in distinct layers and/or they can be comingled such that their distinctive properties are more blended from one region of a nanomembrane to another. In one embodiment, nanomembranes can be a polymer formed by polymerization from a precursor material of monomers due to direct/indirect electrochemical reactions on suitable electrodes. In other embodiments, the nanomembrane(s) can be nanomembranes having metal material electrochemically accumulated on one or more primary electrodes from precursor materials, for example, but not limited to, metal ions and/or doping agents.

To form a nanomembrane by electrochemical deposition, a reaction solution, in embodiments, containing one or more precursor materials such as monomers and/or ionic materials, and/or doping agents, can be introduced as a solution in contact with one or more primary electrodes. Solutions largely comprised of organic and/or aqueous solvents can be used to deliver the monomers, ionic materials, and/or doping agents. By imposing electrical stimuli at the one or more primary electrodes, one or more nanomembranes can be tunable manufactured by an electrochemical action thereon. Electrical stimuli imposed at one or more secondary electrodes also may be used to contribute to the deposition of nanomembrane(s) on a primary electrode(s).

As disclosed herein, nanomembrane(s) can be tunably formed, e.g., in an electrochemical deposition, by tuning various manufacturing parameters including, without limitation, the electrical stimuli used for electrochemical reactions occurred on the electrode(s), number of cycles of the electrochemical reactions, and reaction time for each cycle, selection of electrodes, selection of precursor materials, and other possible parameters during manufacturing. As a result, the tunably formed nanomembrane(s) can have tunable amount, tunable dimensions, and/or tunable properties and functions (e.g., depending on selected monomers and/or metal ions) for the electrochemically deposited material(s) on corresponding electrode(s).

Various precursor materials, in embodiments, monomers and/or derivatized monomers, and/or ionic materials and/or doping agents, can be chosen for the properties that they impart by their chemical reactivity in the electrochemistry reactions and/or for the properties and functions they impart on the resulting nanomembranes that they form. Non-limiting examples of electroactive membrane precursor materials can include the following without limitation:

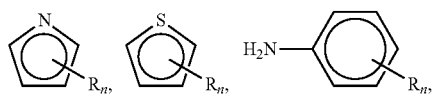

etc.

Depending on the selection(s) of the $R_n$ substituent(s) used, for example as provided in the in each of the above listed embodied materials provided herein, the resulting electrochemically deposited nanomembranes can be for example caused to have properties such as their being hydrophobic, hydrophilic, charged, chemically reactive, metal-binding, metallic, and/or combinations thereof. In one embodiment, Rn can be hydrogen. A wide spectrum of electrochemically driven reactions for forming polymers that can be nanomembranes as described herein are known in the art. The following embodiments are provided as examples only and in no way are limiting to what can be accomplished by electrochemistry-driven deposition reactions to form the apparatus herein.

Non-limiting examples of electroactive membrane precursor materials that can be acted on by direct and/or indirect electrochemical reactions to generate a hydrophobic nanomembrane can include, in embodiments, polymer precursor(s) with one or more substituents such as saturated and/or unsaturated hydrocarbons of sufficient carbon-chain lengths to provide a given desired hydrophobicity. Such substituents can be the same or different, and that they need not all confer hydrophobic properties, or the same hydrophobic properties.

Non-limiting examples of precursor materials that can be acted on by direct and/or indirect electrochemical reactions to generate a hydrophilic nanomembrane can include in embodiments, polymer precursor(s) with one or more substituents such as hydroxyls, carboxylic acids, sulfonic acids, thiols, polyethylene glycols, and/or amines which can be used to provide a given desired hydrophilicity. Such substituents can be the same or different, and that they need not all confer hydrophilic properties, or the same hydrophobic properties.

Non-limiting examples of precursor materials that can be acted on by direct and/or indirect electrochemical reactions to generate a charged nanomembrane can include, in embodiments, polymer precursor(s) with one or more substituents such as hydroxyls, carboxylic acids (and/or their salts), sulfonic acids (and/or their salts), thiols, and/or amines which can be used to provide a given desired charge due to their ionization, or lack thereof, when placed in a buffer of a buffer at a given pH. In embodiments, amine-containing substituents in some types of nanomembranes can be made to have a net positive charge in a given buffer, while carboxylic acid-containing substituents in some types of nanomembranes can be made to have a net negative charge in the same or other buffers. Such substituents can be the same or different, and that they need not all confer the charge properties, or the same charge properties.

Non-limiting examples of electroactive nanomembrane precursor materials that can be acted on by direct and/or indirect electrochemical reactions to generate a chemically reactive nanomembrane can, in embodiments, polymer precursor(s) with one or more substituents that can be reactive functional groups such as hydroxyls, carboxylic acids, esters and activated esters, aldehydes, ketones, halogens, sulfonate esters, thiols, azides, alkenes, alkynes, phosphenes, and/or amines which can be used to provide a given desired chemical reactivity. Such substituents can be the same or different, and that they need not all confer chemical reactivity, or the same chemical reactivity. The resulting chemically reactive nanomembranes can further be used as an interface, in embodiments, functioning for attaching secondary molecules thereto.

Non-limiting examples of electroactive nanomembrane precursor materials that can be acted on by direct and/or indirect electrochemical reactions to generate a metal ion binding nanomembrane can include, in embodiments; polymer precursor(s) with one or more substituents such as thiols which can be used to provide a given desired gold-ion ($Au^+$) binding capability. Such substituents can be the same or different, and that they need not all confer metal ion binding activity, or the same metal ion binding activity.

Other non-limiting examples of precursor materials that can be acted on by direct and/or indirect electrochemical reactions to make metalized nanomembranes can include metal ions. The metal ions can be contained in a solution and then deposited onto an appropriately charged primary electrode such that a thickening metal layer forms on that electrode. Such a process is sometimes referred to in the art as being a form of electroplating. In embodiments, by applying appropriate electrical stimuli at the primary electrode(s), the electrochemically deposited metal can form the nanomembranes. The disclosed metal deposition can be driven with substantially the same apparatus and methods that are required for the electrochemical polymerization and/or nanomembrane electroactivity reactions described herein. Possible difference without limitation can be whether certain organic chemicals are included in a given reagent formulation for synthetic membrane polymerization reactions, or instead a given metal ion reagent formulation is used for electrochemical deposition. In embodiments, metallic nanomembrane can be deposited including, but not limited to, metal depositions such as silver, gold, platinum, titanium, copper, iron, tungsten, aluminum, etc.

In embodiments, doping agents also can be included in the electrochemical or non-electrochemical deposition of nanomembranes. The doping agents can be added to a reaction mixture containing precursor materials. The doping agents may or may not directly participate in the electrochemical reaction and may just be 'entrapped' in any manner within the resulting nanomembrane as it is being deposited. The doping agents can include, but be not limited to, molecules that enhance or limit the electrical conductivity of the nanomembrane (in embodiments, ions such $H^+$, $K^+$, $SO_4^-$, $Cl^-$, $NO_3^-$, $Cl^-$, $I^-$, $ClO_4^-$, $PF6^-$, sulfonic acids, protic acids, benzoic acids, malonic acid, metal ions, metal ions in chemical coordination elements such as cobaltabisdicarbollide); molecules that impart sites for chemical reactivity that are not otherwise present in the bulk nanomembrane (in embodiments, thiols, carboxylic acids, hydroxyls); molecules that cross-link or otherwise increase the mechanical strength or durability of the nanomembrane and/or increase or decrease the permeability of the nanomembrane to selective ions, hydrophobic/hydrophilic molecules, proteins, etc. (in embodiments, hydroxyethers, phenolic resins); and/or molecules which increase or decrease the ability of the nanomembrane to be effectively examined via microscopy (in embodiments, for example, but not limited to the use of doping with contrast agents such as metals and metal ions to aid in accommodating scanning and transmission electron microscopy examination methods; doping with UV, visible light, infrared, fluorescent dyes, and/or quantum dots to aid in accommodating light microscopy examination methods).

Note that electroactive nanomembranes deposited by means other than electrochemically-based methods also can include materials like those described that impart properties such as hydrophobicity, hydrophilicity, charge, chemical reactivity, and/or combinations of these. In embodiments, these methods include, but are not limited to, methods such as spraying, vapor-phase deposition, sputtering, spin coating, precipitation, in situ polymerization by electrochemical or non-electrochemical means such as heat- and/or photo-curing, multilayer deposition with the well layer being a sacrificial material that is etched away to create a material membrane over a well, etc.

Any combination of the above mentioned precursor materials, ionic materials, and/or doping agents, can be utilized to achieve the given desired mechanical, chemical and/or electrical properties of resulting nanomembranes, whether deposited by electrochemical or non-electrochemical means. Furthermore, these combinations may be employed such that the properties are generally uniform within and/or at the surface of a given nanomembrane. Nanomembranes also may be formed such that the properties are non-uniformly distributed within and/or at their surface. As another non-limiting embodiment, a nanomembrane can be deposited such that the portion of its deposited material that is closest to the primary electrode(s) upon which it is formed can have one general property in embodiments (e.g., being hydrophobicity, uncharged, and/or chemically unreactive), while the portion that is furthest away from the primary electrode(s) has a different property (e.g., being hydrophilic, charged and/or chemically reactive). In embodiments, non-uniform distributions of nanomembrane properties can be formed in, but are not limited to, layers, patches, gradients, etc. Furthermore, these properties can be made to change in their distribution and/or qualities over time via, for example but not limited to: imposing electrical stimuli that results in the electrochemically-driven addition, removal, and/or modification of the nanomembrane's material; adding or removing material from the nanomembrane via coatings, derivatizations, and/or extractions of materials from the deposited polymer; imposing electrical stimuli via one or more primary and/or secondary electrodes so that the nanomembrane(s) structure changes in dimensionality and a patch or layer of material possessing a given quality is covered up or becomes exposed.

The nanomembranes, whether deposited by electrochemical or non-electrochemical means, can be deposited to have electrical properties, for example, providing electrical conductivity; capable of driving an electrochemical reaction that enables molecule attachment via chemistries; capable of driving indirect chemical reactions, etc. Specifically, electrically conductive nanomembranes can allow passage of electrons in a manner that is functionally similar to the way that electrons flow through a metal wire. This property may allow the nanomembranes to be used as an electric sensor surface for sensing the nanomembrane or for sensing at subsection(s) of the nanomembrane such as at points or projections on the surface, for sensing at growth-plates of a nanomembrane's surface, etc. Nanomembranes can be capable of driving an electrochemical reaction that enables molecule attachment via chemistries including oxidation and/or reduction reactions of materials for functionalization.

Nanomembranes formed to be capable of driving indirect chemical reactions of, e.g., 1,4-benzoquinone reaction, can be provided by way of that enable production of acidic or basic solutions at specific places along a nanomembrane's surface. These acidic or basic solutions can in turn be used to catalyze subsequent chemical reactions, including but not limited to, the attachment of molecules such as proteins, enzymes, antibodies, lectins, peptides, amino acids, modified amino acids, lipids, nucleic acids (single and double stranded DNAs, RNAs, aptamers), nucleic acid components (nucleosides, nucleotides, methylated/modified versions of the same), ionized salts, small molecules, drugs, etc, and combinations thereof. These acidic and basic solutions also in turn can be used to catalyze subsequent chemical reactions, including but not limited to, the attachment of cross-linking agents on these points of a nanomembrane's surface, which in turn can be used as points of attachment for other molecules.

Nanomembranes can be synthesized to be relatively hydrophobic such that materials like lipids can associate with them, and/or they can support formation of a lipid layer (a monolayer or a bilayer) across a nanomembrane's nanochannel. Hydrophobic nanomembranes can enable insertion of, e.g., proteins, to form membrane-associated proteins.

Nanomembranes can be synthesized that chelate, coordinate, and/or bind metal ions such that the nanomembrane becomes metalized. Following this, an electrical current can be applied via one or more primary electrodes upon which it is formed, and/or via one or more secondary electrodes, so that electrical stimuli can be imposed on the nanomembrane. These electrical stimuli can be used to drive other chemical reactions. Furthermore, the nanomembrane material can be chosen such that its structure is not disrupted by imposed electrical stimuli. In embodiments, materials can be used for nanomembrane formation that require high threshold electrical stimuli to induce a dimensional change so that 'lower' electrical stimuli can be imposed on it without causing any dimensional change to it.

The disclosed device can include one or more nanomembranes formed on desired electrodes of the nanowells/nanotubes. Each of the one or more nanomembranes can have the same or different desired properties and functions. The one or more nanomembranes can be generated by simultaneous and/or sequential electrochemical or non-electrochemical depositions. The one or more nanomembranes can be either homogeneously or heterogeneously mixed in one single layer and/or non-uniform layers, regions, gradients, etc of nanomembranes during its formation. For example, a two-layer nanomembrane configuration can include a first nanomembrane that is electrochemically or non-electrochemically formed on an electrode and a second electroactive nanomembrane formed on the first nanomembrane. Note that the number of materials and layers of nanomembranes are not limited and any number of materials/layers and can be formed on an electrode to provide desired properties, functions, and tunable nanochannels or nanopores formed by the electroactive nanomembrane.

In one embodiment, a method of forming multiple nanomembranes can include steps, for example, forming the first nanomembrane over the exemplary electrode using a first precursor material selected in any suitable deposition processes, introducing a different precursor material, or replacing the first precursor material (that forms the first nanomembrane) with a second precursor material during a deposition process of the second electroactive nanomembrane. The second electroactive nanomembrane can have desired properties and functions that are the same or different than the first nanomembrane. Each of the first nanomembrane, the second electroactive nanomembrane, and/or any additional nanomembranes formed over the corresponding electrode can be the same or different, for example, each can be hydrophobic, hydrophilic, chemically reactive, metal-binding, charge-binding (negative or positive ions), metallic, etc.

In one example, an exemplary device can include a first nanomembrane that is dense, non-conductive, and/or chemically unreactive. The second electroactive nanomembrane formed over the first nanomembrane and can be, for example, porous, conductive, and/or chemically reactive, as compared with the first nanomembrane. In another example, functionalizations can be performed to the surface of the electroactive nanomembrane of the formed nanochannel/nanopore.

In embodiments, nanomembranes are deposited such that the material that is in close proximity to where a nanopore is positioned with it has chemical properties that are substantially different from the bulk of the rest of the nanomembrane. This can be accomplished by using the non-electrochemical and/or non-electrochemical means. Non-limiting examples of methods to accomplish this include employing non-electrochemical methods such as spraying or sputtering of the 'bulk' of a nanomembrane with one material and then adding a thin layer of another material to form a lip or edge that is in close proximity to the nanopore's opening. Electrochemical means also can be used to polymerize the 'bulk' of a nanomembrane with one material, and then switching to a different material to electrochemically deposit a thin nanomembrane coating that creates the sidewall of a nanopore. The electroactive properties of the nanomembranes described herein also can be used, for example imposing electrical stimuli on a nanomembrane(s) such that their dimensionalities shift to form a nanopore with its sidewall composed of materials that is/are functional different than the remaining 'bulk' of the nanomembrane. Combinations of electrochemical, non-electrochemical, and/or nanomembrane electroactivity induction methods are also possible examples of creating nanopore sidewalls that have functional properties that are distinct from that of the bulk membrane. Regardless of the method(s) used to create them, these types of nanomembrane nanopores can be utilized in a range of embodiments. As one non-limiting embodiment, for example, this method can be used to provide for nanopores with sidewalls that are dimensionally tunable by imposed electrical stimuli while the bulk membrane is not dimensionally tunable. This approach can provide particularly fine control over the electrical stimuli-induced dimensionality of a given nanopore's sidewall. In embodiments, this approach also can be used to localize functionalities such as a specific type of chemical reactivity in close approximation to a given nanopore. A non-limiting example of this is to create a nanomembrane such that chemical attachment points for functionalizations (e.g., antibodies, proteins, enzymes, nucleic acids, etc.) are located only in close proximity to a given nanopore.

As described herein, electronic circuitry can be used to induce dimensional changes at a given deposited nanomembrane. Electronic circuitry also can be utilized to electrochemically deposit electroactive material at a given primary electrode. In embodiments, the tunable manufacturing of nanomembranes with desired properties and/or functions also can be monitored during its fabrication by using circuitry that is electronically connected to one or more primary and/or secondary electrodes. The electrode circuitry can be configured for monitoring the generation of the nanomembrane and/or monitoring the flow of analyte molecules (in embodiments, ionic material) through the resultant nanochannel in the nanomembrane. The monitoring process can be carried out by taking measurements via one or more primary and/or secondary electrodes, including sensing through the nanomembrane itself. Such measurements can include, but are not limited to, measurements such as current, resistance, voltage, capacitance, and/or combinations thereof. Measurements also may be made to monitor the accumulation of ionic material and/or any other constellation of molecules at the electrode(s) and/or at the nanomembrane itself, including monitoring for molecules that bind to and/or react with the nanomembrane(s) and/or one or more primary and/or secondary electrodes in the apparatus. In embodiments, by applying a voltage or a current to one or more primary and/or secondary electrodes, the electrical resistivity provided by a given nanomembrane can be measured. These measurements also can be used to monitor and/or control the electrochemical deposition process and dimensionalities of a given nanomembrane anytime during and/or after their manufacture.

FIG. 1 is a schematic of a portion of an exemplary device including a nanowell array according to various embodiments of the present teachings. The nanowell array in FIG. 1 can include a plurality of nanowells 105 or nanotubes when the bottom of the nanowell is not included. The nanowells 105 can be provided in a solid support material 108, for example, a semiconductor solid support material or any suitable semiconductor materials used for an integrated circuit (IC) device, where standard semiconductor manufacturing techniques can be generally used. The support material 108 can be suitable for integrating nanowells, nanotubes, nanomembranes, and/or bio-species therewith. The semiconductor material 108 can have a rigid or semi-rigid surface or surfaces 109. One or more sidewall electrode(s) 130, 132, 134, 136 are included for an exemplary nanowell 105, which can further include a bottom electrode 112, for example.

Figures 2A, 2B, 2C:
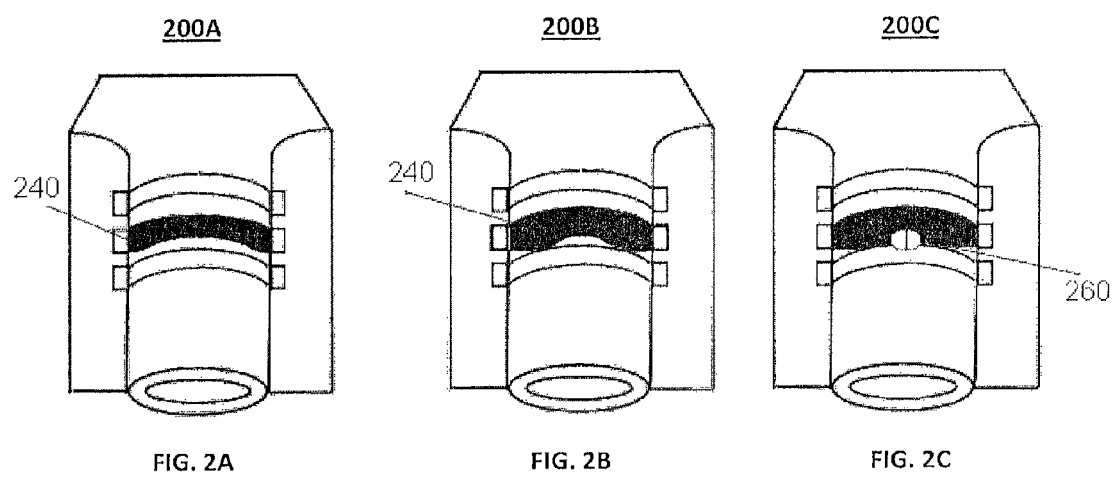
FIGS. 2A-2C are schematics showing nanomembrane deposition using one or more materials and tunability on sidewall of an exemplary nanowell according to various embodiments of the present teachings.

FIGS. 2A-2C are schematics showing nanomembrane deposition on sidewall of an exemplary nanowell according to various embodiments of the present teachings. As shown in FIG. 2A, the device 200A can include an exemplary nanowell having one sidewall electrode deposited with a nanomembrane 240. The nanomembrane can be deposited with various material deposition techniques as disclosed herein. The deposition can be electrochemically-induced or non-electrochemically-induced. The nanomembrane 240 can be an electroactive nanomembrane regardless of the deposition techniques used. In FIG. 2B, the nanomembrane 240 can further be deposited having desired thickness on the associated electrode. In FIG. 2C, a second nanomembrane layer 260 can be, for example, electrochemically deposited over the first nanomembrane 240 in response to suitable electrical stimuli such as a voltage or current applied to the associated electrode or otherwise applied to the first nanomembrane 240. In embodiments, this second nanomembrane layer can, for example, be composed of a material that has distinct properties compared to the first layer of nanomembrane. It also, for example, can be a layer that forms a thin coating as the sidewall of a given nanopore.

The disclosed apparatus/devices and methods can be used for a wide range of applications. The following only are examples of such applications, and these in no way limit the range of other applications for which the apparatus and/or methods provided herein.

As used herein, an "analyte" is one or more molecules included, but not limited to molecules such as proteins, enzymes, antibodies, lectins, peptides, amino acids, modified amino acids, lipids, nucleic acids (single and double stranded DNAs, RNAs, aptamers), nucleic acid components (nucleosides, nucleotides, methylated/modified versions of the same), ionized salts, small molecules, drugs, and/or combinations thereof. Larger analytes are also possible including quantum dots, beads, particles, vesicles, liposomes, subcellular particles (e.g., nuclei, endosomes, mitochondria, endoplasmic reticulum, lysosomes, Golgi, ribosomes, protein complexes, protein/nucleic acid complexes) cells, viruses, bacteria, mold, fungi, and/or combinations thereof, without limitation to the resulting dimensionalities of the assemblages. Analytes can be provided in a wide spectrum of formulations. In embodiments, they can be provided in organic and/or aqueous solutions, in gases, in/on particles, etc., in mixtures, and/or combinations thereof.

In one set of embodiments, the apparatus and methods described herein can be used without limitation for applications that include ones which enable the preparation, separation, partitioning, filtration, exclusion, inclusion, combination, reaction, binding, unbinding, isolation, etc. of one or more analytes, processes which can be carried out separately and/or in combination and which are collectively referred to herein with respect to analytes-related processes as being analyte "interactions" with nanomembranes. Thus, analytes generally are described herein with the terminology that they are being caused to interact with a nanomembrane. However, it should be understood that analytes can in fact be caused to interact with any number of nanomembranes at any given time according to the same terminology. Similarly, it should be understood that analytes can be caused to "move" within a nanochannel as defined herein, whether this nanochannel contain a nanomembrane(s) or not, and that this same terminology also describes that analytes can be caused to "move" in within any number of nanochannels over a given time.

Analytes and other molecules can be made to "move" a nanochannel by a number of methods. In embodiments, the molecular motion of analytes can be passive Brownian motion-driven diffusion. Such passive diffusion generally can be enhanced or slowed by raising or lowering the temperature of the solution or gas containing the analyte(s), respectively. Temperature control can be provided by heating and/or cooling elements on or around a solid support(s), chamber, pumping system, environmental control system, etc. employed for given application.

It also is possible in embodiments to impose electrical stimuli such as, but without limitation, a voltage or current across a given nanomembrane such that analytes and other molecules are subjected to electrophoretic forces that can move them towards, away from, and/or through a given nanochannel. For analytes and other molecules to be electrophoresed under such conditions, they need to bear at least a transient or net charge, either positive or negative in sign such that they are attracted to the electrode(s) with an opposite polarity and repelled from the electrode(s) of the same polarity. Such analyte motion can for example be created by electrically polarizing one or more of the available electrodes "above" a given nanomembrane in a nanochannel such that it, or they, are opposite in polarity (i.e., to be positive or negative in sign, such as to serve as a cathode or anode) to the polarity of the one or more electrodes below this nanomembrane. The same or different voltage can be imparted on each nanochannel's nanomembrane(s) as desired, even as they occur in a given nanotube and/or nanomembrane. Such electrical stimuli may be invariant and/or may vary in wave dimensionality, amplitude, frequency, duration, etc., and combinations thereof. These variations may be recurrent, or may also vary over time. The analyte motion-inducing electrical stimuli may be utilized to cause the electrophoresis of the exemplary analyte(s) into or out of a given nanochannel at a given rate, for example, but without limitation, by applying a higher bias voltage to cause a given type of analyte to move into or out of the nanochannel(s) at a faster rate than can be accomplished by the application of a lower bias voltage. Analyte motion-driving electrical stimuli also can be transiently alternated in sign to reverse the course of an ionized molecule, which has become lodged in, or plugged a nanochannel. Similarly, such electrical stimuli can be reversed for a period of time, for example to drive ionized molecules out of a nanowell to diminish a concentration gradient formed there following a period in which such ions previously have been electrophoresed into a given nanowell. Likewise, such electrical stimuli can be reversed for a period of time to drive ionized molecules from one or more chambers connected by a given nanotube such that they are moved to the one or more other chambers at the other end of a given nanotube. Note, too, that a electrical stimuli-driven analyte movement also can be used to move analytes within a given nanochannel. In embodiments, imposed electrical stimuli can be utilized to move molecules from the bottom of a nanowell to one or more sidewall electrodes, to move molecules from one portion of a sidewall to another, to move molecules from one nanotube to another, from one nanotube to one or more nanowells, etc. The apparatus and methods in the art regarding capillary electrophoresis, capillary zone electrophoresis, and gel electrophoresis can be utilized to enable these types of embodiments to move analytes by electrophoresis. These electrophoretic forces also can be utilized to 'push' or 'pull' analytes and other molecules from within one or more chambers and into one or more nanochannels. For example, in embodiments, electrical stimuli can be imposed at one or more bias electrodes such that these stimuli are 'paired' with one or more sidewall or bottom electrodes in the case of a nanowell, or one or more sidewall or bias electrodes at the opposite end of a nanotube in the case of a nanotube. Such a pairing including imposing electrical stimuli such that the members of the pairing are opposite in sign (i.e., the electrode(s) including one 'side' of the pairing has a positive sign/polarity, while the other electrode(s) including the other side of the pairing has a negative sign/polarity). Such a pairing can be utilized to attract or repel ionized analytes possessing a positive or negative charge to generally flow towards electrode(s) side of the pairing of the opposite sign/polarity. This embodiment describing the ability to attract or repel charged analytes and other molecules towards or away from nanochannels, whether containing nanomembranes or not, is referred to herein as using imposed electrical stimuli to create an "ion funnel current/voltage." In the embodiments in which an ion funnel current/voltage is also being utilized to draw analytes and other molecules from a chamber and past or through a given nanomembrane, one of the electrode(s) comprising an ion funnel current/voltage pairing is placed 'above' the nanomembrane and the other electrode(s) comprising the other ion funnel current/voltage pair is placed 'below' the nanomembrane.

A wide spectrum of technologies in the art also can be used to generate mechanical pressure to move analytes across the surface of, or through, a given nanomembrane. In embodiments, mechanical pressure that moves analytes can be provided by the use of pumps, vacuums, pressurized liquids, pressurized gases, centrifugation, etc., and combinations thereof. The apparatus and methods in the art regarding liquid chromatography including low pressure, high performance/HPLC, filtration, and the like are generally appropriate to move analytes in liquids. In other embodiments, the apparatus and methods in the art regarding gas chromatography and the like are generally appropriate to move analytes in gases.

Making use of the electrically tunable dimensionality capabilities of a given nanomembrane is another means by which analytes can be moved across its surface(s). In embodiments, a given nanomembrane can be subjected to oscillations of imposed electrical stimuli such that it 'stirs,' or otherwise moves around in, a given solution or gas. Similarly, groups of nanomembranes can be subjected to imposed electrical stimuli oscillations such that they generally 'sweep' or otherwise move analytes, including in a pulsatile, peristaltic, and/or wave-like fashion, across or through a given nanomembrane or nanochannel.

It should be understood that these modes by which analytes can be induced to move through a nanochannel can be subjected to significant modulation as desired. Thus, in embodiments, analyte movements with respect to a given nanomembrane can be induced to be essentially unidirectional, bidirectional/reversible, random, etc., and combinations thereof, and these movements also can be varied in their force, frequency and duration as is desired for a given application. Furthermore, in embodiments, analytes can be moved utilizing just one, or combinations of two or more, of the analyte motion-inducing apparatus and methods described herein.

In embodiments, a wide variety of combinations of one or more electrically tunable nanomembranes with one or more possible modes to induce analyte motion into, within, and/or through a given nanochannel provide for useful applications. These include, but are not limited by, the following examples.

In embodiments, one or more nanomembranes within a nanochannel can be arranged to form a barrier such that only analytes of a sufficiently small size can pass through the nanochannel that they form. Barriers comprised of nanomembranes of a given charge (in embodiments, bearing positively or negatively charged molecules) can also be constructed such that they only provide for a relatively unhindered passage of similarly charged analytes, while analytes of a charge opposite to such nanomembranes are retarded and/or rendered immobile. Similarly, nanomembranes can be constructed of a given degree of hydrophobicity or hydrophilicity such that they do or do not retard the flow of, or otherwise render immobile, molecules of an appropriate hydrophobicity or hydrophilicity.

Nanomembranes can be constructed in a given nanochannel and then subjected to an appropriate imposed electrical stimuli at the primary and/or secondary electrodes in and around the nanochannel such that a pH/charge gradient is formed from one portion of the nanochannel to another. Analytes moving within such a gradient, especially when under electrophoretic forces, can become immobilized in the portion of the nanochannel in which their charge is effectively neutralized (i.e., when a given analyte moves to a position in the nanochannel that matches its isoelectric point). The apparatus and methods in the art regarding isoelectric focusing can be utilized to enable these types of embodiments.

A given nanomembrane also can be functionalized to bind passing analytes. In embodiments, they can be functionalized with molecules such as antibodies, antibody fragments, aptamers, lectins, phage, etc., such that passing analytes can be retarded, or rendered immobile, under appropriate conditions.

A given nanomembrane also can be modified with chemically reactive molecules such that they act on an appropriate analyte as it passes. In embodiments, a nanomembrane can be modified with enzymes, reactive chemicals, etc. such that they exert a chemical reaction upon passing analytes under appropriate conditions.

A given nanomembrane can be constructed such that it carries out more than one desired functionality, or combinations of functionalities, at a given time. In embodiments, a nanomembrane can be constructed such that it binds analytes of a given charge while it also blocks the passage of analytes over a given size. A great many other combinations of functionalities are also possible in embodiments.

The apparatus and methods described herein also can be employed to modify a given nanomembrane's tunable properties. In embodiments, a given nanomembrane can be controllably altered in its dimensionality in real-time, stepwise, and/or spread over a continuum or gradient such that molecules of increasingly larger or smaller size are allowed to pass through a given nanochannel. Similarly, a given nanomembrane's charging, hydrophobicity, hydrophilicity, etc., can be changed to affect how analytes interact with it over time.

By changing the properties of a given nanomembrane in electrically tunable manner, it also is possible to unbind (elute) analytes that have become bound to it. Such methods can be gradated via electrical stimuli-induced changes that are stepwise, spread over a continuum or gradient, etc. such that they enable analytes to become unbound in specific groupings and/or isolated from other groupings. In embodiments, such methods can include the induction of an electrochemical reaction such that analytes are unbound as a nanomembrane is caused to depolymerize. A nanomembrane also can be electrically induced to change shape such that analytes are released.

The apparatus and methods described herein also can be used to cause analytes to unbind via electrophoretic forces. In embodiments, by imposing electrical stimuli at the primary electrode(s) upon which the nanomembrane is deposited (i.e., electrophoretic forces that are provided via conductance through a given nanomembrane) and/or one or more secondary electrodes in the apparatus, analytes can be subjected to sufficient forces such that they become unbound from the nanomembrane.

Analytes also can be made to unbind from a given nanomembrane by the application of a suitable fluid to release them (or gas, or combinations thereof). Charged analytes generally can be unbound from charged nanomembranes and/or nanomembranes modified by proteins, aptamers, and the like via the application of a solution containing ionized molecules (in embodiments, an aqueous solution containing dissolved salt). Similarly, analytes generally can be unbound from hydrophobic and/or hydrophilic nanomembranes via the application of a solution containing hydrophobic/hydrophilic molecule stabilizing/solubility agents (in embodiments, ethanol, dimethylsulfoxide, detergents, salts). Such methods can be gradated in embodiments, using agents that are added stepwise, spread over a continuum or gradient, etc. such that they enable analytes to become unbound in specific groupings and/or isolated from other groupings. In embodiments, the apparatus and methods in the art regarding ion exchange chromatography, including low pressure, high performance HPLC, filtration, etc, in particular can be utilized to enable these types of applications in which charged analytes are being unbound. In embodiments, the apparatus and methods in the art regarding reverse phase chromatography, including low pressure, high performance/HPLC, filtration, etc., in particular can be utilized to enable these types of applications in which hydrophobic and/or hydrophilic analytes are being unbound.

Changing the temperature of a nanomembrane (or the solution or gas or combinations thereof that are passing over the nanomembrane) can also be used to unbind some analytes. Such methods can be gradated in embodiments, via direct heating and/or electrical stimuli-induced changes that are stepwise, spread over a continuum or gradient, etc. such that they enable analytes to become unbound in specific groupings and/or isolated from other groupings.

Changing the mechanical pressure applied to a given nanomembrane also can be utilized to unbind analytes from a given nanomembrane. This can be accomplished by adjusting the settings on the pumps, vacuums, etc. that are used to generate mechanical pressure in order to increase or decrease the pressure being applied on a given nanomembrane.

A wide variety of apparatus and methods can be employed to monitor the analytes that are applied to, pass through, are bound by, and/or are unbound from a given nanomembrane described herein.

Analyte interactions with a given nanomembrane, including all of the transients and/or binding interactions described herein, can be monitored directly by the apparatus and methods described herein in embodiments. In one type of embodiment, the electrode circuitry for one or more primary and/or secondary electrodes can be configured to monitor changes in the electrochemical capabilities and/or tunable dimensionalities of a given nanomembrane that result from interactions with analytes (e.g., in embodiments to monitor changes in an imposed electrical stimuli's ability to induce a modification in a given nanomembrane's polymerization, depolymerization, composition change, dimensionality, etc, as described herein, that indicates a nanomembrane's interactions with analytes will, are, or have been occurring). The interaction of analytes also can be monitoring via taking measurements through one or more electrode(s) in the solid support, including sensing through the nanomembrane itself, and/or via one or more electrodes located elsewhere (i.e., in a chamber). In embodiments, analyte interaction monitoring modes at a given nanomembrane can include, but are not limited to, measurements such as current, resistance, voltage, and/or capacitance through the nanomembrane and/or at one or more of any sidewall, bottom, bias, primary, and/or secondary electrodes in the apparatus, and/or any combinations of the above. The monitoring of analytes via the accumulation of charged analytes, ions and/or any other constellation of molecules at one or more electrodes in the apparatus and/or at a given nanomembrane itself also are possible in embodiments. In embodiments, monitoring also can be conducted via the reaction of analytes and/or any other constellation of molecules at one or more electrode in the apparatus, and/or at a given nanomembrane. By imposing electrical stimuli to one or more electrodes in an apparatus, the electrical resistivity of a given nanomembrane interacting with analytes can be measured in related embodiments. The flow of analytes as determined by modulations in the requirements of an apparatus' electronics to provide for an "ion funnel current/voltage" through a nanomembrane's nanopore is another means by which analytes can be monitored for their nanomembrane interactions in embodiments.

In embodiments, one or more electrodes made of, or covered by, silver is placed 'below' a nanomembrane(s) past which an ion funnel current/voltage is imposed. The ion funnel current/voltage is then configured to drive negatively charged chloride (Cl—) ions 'down' towards the silver electrode(s). As the chloride ions contact the silver surface, the well-known silver/silver chloride reaction can ensue such that an electron density develops at that electrode. The development of this electron density can be monitored for example, but not limited by, the numerous current and/or voltage measuring devices that also are well known in the art. The ion funnel current/voltage also can drive negatively charged analytes 'down' past the nanomembranes, and positively charged analytes 'up' past the nanomembranes. The flow of negatively and/or positively charged analytes can affect the movement rate, and/or count, of chloride ions that are driven towards the silver electrode over a period of time, particularly as might be crowded together in the confined space of a nanochannel or nanopore. In embodiments, these effects can result in characteristic signal modulations that have, for example, been used to identify specific types of DNA nucleotides as they flowed sequentially through a protein nanopore (Clark et al., Nat. Nanotechnol 2009).

Thus, this chloride/silver/silver chloride measuring system enables one particular mode of embodiments for measuring the flow of analytes past nanomembranes.

A wide spectrum of other instrumentation and methods, which can be used in combination(s) with the apparatus and methods described herein, also can be used to monitor analytes interacting with a given nanomembrane. For example, samples of an analyte formulation can be taken before and after they have been applied to the nanomembrane-bearing apparatus described herein to determine what analyte(s) may have been removed, added, or remain unchanged in concentration and/or composition as a consequence of their interactions within the nanomembrane. Such sampling in embodiments can be carried out by extracting materials from the one or more chambers 'before' and 'after' an analyte formulation has been moved through one or more nanomembrane-deposited nanochannels in nanotubes, and/or by extracting materials from 'above' and 'below' one or more nanomembrane-deposited nanochannels. In embodiments, samples also can be taken from within a given nanochannel, including sampling a given nanomembrane in the nanochannel. In embodiments, samples can be taken from the material comprising the electrode(s), solid support(s), chambers, and/or sidewalls in a given apparatus. In embodiments, samples also can be taken from any of the gas- and/or fluid-filled spaces in a given apparatus (i.e., taking samples from the spaces in the chamber(s), nanowell(s), and/or the nanochannel(s) of an apparatus). The sampling of these spaces can be carried out via one or more ports manufactured to provide access to them, and/or by gaining access by force through a given chamber wall, solid support, sidewall, and/or nanowell bottom. In any case, analytes can be analyzed for their composition and/or quantitated via whichever of the many well-described instruments and methods in the art are most appropriate. For example, in embodiments, such analyte monitoring instruments can include, but are not limited to: spectroscopy (nuclear magnetic resonance, Raman, surfaced enhanced Raman, fluorescence, ultraviolet, luminescence, visible light, X-ray, X-ray photoelectron, infrared, terahertz, atomic force), flame ionization, surface plasmon resonance, surface acoustic wave, antibody-based, ELISA, peptide-based, lectin-based, enzyme-based, peptide/protein sequencing, nucleic acid/oligomer sequencing, lipid-based, small molecule-based, optical wave guide-based, MEMS-based, pulsed amphometric detection, nephelometry, circular dichroism, X-ray diffraction, radiochemical detection, mass spectrometry, and/or combinations thereof.

The electroactive nature of the nanomembrane provided herein also enables embodiments for the directly tunable, real-time control over the cross-sectional area of a nanochannel that is occupied by a given nanomembrane in a nanotube or nanowell. One embodiment for such nanomembranes is that they can be employed as real-time dimensionally tunable structures to create size-oriented barriers and/or sieves for analytes that can be made to move around, over, and/or through the nanomembrane(s) surface. As one non-limiting example of this embodiment, one or more nanomembranes can be deposited in a nanotube such that they initially allow only comparatively small analytes (e.g., small ions, nucleic acids, amino acids, solvated small molecule drugs, etc.) to move unhindered through the nanochannel. By imposing appropriate electrical stimuli on the nanomembrane(s), a dimensional change can be induced in real-time such that now larger analytes (e.g., peptides, nucleic acid oligomers, etc.) can be caused to move unhindered through the nanochannel. By imposing yet other appropriate electrical stimuli on the nanomembrane(s), now even larger analytes (proteins, aptamers, etc.) can be moved through the nanochannel. Thus, the apparatus described herein can be utilized to create a device that separates analytes according to their size, and that this capability can be modulated in real-time.

Dimensional changes also can include changes in the molecular composition of a given nanomembrane can according to the apparatus and methods described herein. For example, in embodiments, electrochemical reactions can be enabled in real-time by applying electrical stimuli at one or more primary or secondary electrodes such that a given nanomembrane is subjected to a polymerization and/or depolymerization reaction(s). A given nanomembrane under such electrical stimuli controls thereby in embodiments can be induced to add or remove molecules, change in its charge, expose/hide portions of itself, etc. such that its surface and/or internal composition can be change in real-time. Such reactions under induced electrical stimuli control, in embodiments, can cause the resulting nanomembrane to become more hydrophobic, hydrophilic, charged, metal binding, and/or combinations thereof. Direct and/or indirect electrochemical reactions also can be utilized to attach or detach materials from the nanomembrane, including functionalization materials such as proteins, enzymes, antibodies, lectins, peptides, amino acids, modified amino acids, lipids, nucleic acids (single and double stranded DNAs, RNAs, aptamers), nucleic acid components (nucleosides, nucleotides, methylated/modified versions of the same), ionized salts; small molecules, drugs, and/or combinations thereof. As one non-limiting embodiment of this, one or more nanomembranes can be deposited in a nanotube such that they initially bind to molecules that have low-to-high negative charge densities. This in a non-limiting example can be accomplished by depositing nanomembrane material(s) that initially bears a dense positive charge at its surface and/or any internally analyte-accessible portions. Analytes of a low-to-high negative charge (for example, but not limited to, small to large nucleic acid oligomers) can bind to this nanomembrane(s) as they are moved through the nanochannel, while positively charged analytes remain unbound and move relatively unhindered through the nanochannel. By imposing appropriate electrical stimuli on the nanomembrane(s), a dimensional change can be induced such the nanomembrane(s) looses a significant portion of its positive charge density (for example, but not limited to, depolymerizing aspect of the nanomembrane that bear positive charge, undergoing an electrochemical reaction that eliminates positive charges without requiring membrane depolymerization, and/or undergoing three-dimensional change that covers up a portion of the nanomembrane's positive charge). This change can result in the analytes with comparatively less negative charge (for example, but not limited to, small(er) nucleic acid oligomers) becoming unbound by the nanomembrane(s) such that they now can be made to move unhindered through the nanochannel. By imposing yet other appropriate electrical stimuli on the nanomembrane(s), now analytes bearing even higher negative charges (for example, but not limited to, large(er) nucleic acid oligomers) become unbound and can be moved through the nanochannel. In another embodiment, a nanomembrane can be deposited such that the same overall methods can be used to separate analytes based on their positive charge using nanomembranes comprised of materials that can be modulated in their negative charge density. Thus, the apparatus described herein can be utilized to create a device that separates, isolates, extracts, etc. analytes according to their positive or negative charge, and that this capability can be modulated in real-time.

In other embodiments, a similar approach can be to create a device that enable analytes to be separated/isolated/purified/extracted/etc, by hydrophobicity, hydrophilicity, functionalization binding, metal binding, chemical reactivity, and properties, too, and be modulated in real time.

In still other embodiments, a similar approach can be undertaken to enable analytes to be separated/isolated/purified/extracted/etc. by two or more of their properties such as their hydrophobicity, hydrophilicity, functionalization binding, metal binding, chemical reactivity, and the like. As one non-limiting example of this, nanomembranes can be deposited so that molecules such as nucleic acid oligomers, antibodies, aptamers, lectins, etc. functionalize them, thereby enabling the binding of analytes of an appropriate type to that nanomembrane. The same nanomembranes can be deposited in a manner such that they at least initially only allow comparatively small analytes to move through the nanochannel(s) with which they are associated. When in use, the nanomembranes in such a device can then be tuned in real time such that they increase or decrease their properties for binding of given analytes even as they are tuned to permit or restrict the passage of analytes according to their size. Other non-limiting embodiments include nanomembranes formed to interact with analytes in combinations such as chemical reactivity and size, charge and size, functionalization and charge, functionalization and hydrophobicity/hydrophilicity, chemical reactivity and charge, and the like.

In another set of embodiments, one or more nanomembranes can be constructed in a nanochannel such that it/they support the formation, stability, and/or destabilization of one or more lipid bilayers. These embodiments also can be used to exclude the incorporation of molecules into lipid bilayers based upon molecular size.

As described herein, "lipid bilayers" generally are composed of lipids (e.g., phospholipids, fatty acids, glycerides, etc.). When these molecules are appropriately combined, they can spontaneously self-assemble into a roughly two-layered structure. In this structure, the lipid molecules are aligned on both sides of the layers so that have their hydrophobic 'tails' oriented towards the bilayer's interior and they have their hydrophilic 'head groups' oriented towards the outer faces of the bilayer. Lipophilic molecules also can be included in, or associated with the surface(s) of lipid bilayers (e.g., cholesterols, amphipathic proteins, hydrophobic molecules, etc, can be 'dissolved' within a given bilayer; various charge-binding molecules, etc. can be coordinated by, or bound to, the lipid head group(s) at the surface of a bilayer).

Lipid bilayers are used for a wide variety of apparatuses and methods in the art, for example ones making use of their ability to provide for a barrier between two aqueous compartments for hydrophilic molecules, to provide for an electrically resistive barrier between two compartments, etc. Lipid bilayers also utilized to provide an artificial structure into which certain membrane proteins can be inserted and tested for their functionalities. Important classes of such membrane proteins include the porins, ion channels/complexes, and protein nanopores. Note that these protein nanopores are distinct from the "nanopores" as defined herein. Protein nanopores are composed of one or more proteins while "nanopores" as defied herein are created by encircling nanomembrane sidewalk. In order to test their functionality, these membrane proteins are generally first inserted into a lipid bilayer. They often then are treated by the addition of a molecule to one side of the lipid bilayer to determine whether this molecule augments or inhibits a basic feature of the membrane protein's functionality (e.g., to determine whether the molecule is an agonist or an antagonist of the membrane protein). A membrane protein's functionality is determined, for example, by how it effects the electrical and/or analyte permeability through a lipid bilayer and/or through the bilayer-spanning protein nanopore formed by a given membrane protein. For example, lipid bylayer-embedded hemolysin protein nanopores have been used as to measure the length of single-stranded DNA molecules (Ayub et al., J. Phys.: Condens. Matter 22, (2010) 454128). Similar systems also have been used to monitor the flow of DNA oligomers through protein nanopores embedded in lipid bilayers (Clark et al., Nat. Nanotechnol 2009). Nonetheless, the utility and robustness of these membrane protein studies are considerably challenged by the generally instability of lipid bilayers. In particular, lipid bilayers are easily disrupted by mechanical shock, thermal motion, and/or the presence of even trace amounts of detergents or organic solvents. Conventional approaches for overcoming these challenges include making use of solid-state nanopores formed by semiconductor fabrication techniques involving focused electron and ion beams to create nanopores in a semiconductor material.

Embodiments of the apparatus and methods described herein can be used to create a greatly stabilized lipid bilayer. Lipid bilayer also can be tuned in their dimensionalities by the electroactive nanomembranes described herein such that they can be made to size-exclude molecules from inserting into their surfaces.

A general feature of these embodiments is that they include one or more nanomembranes being deposited on a given nanochannel's sidewall, and which are generally hydrophobic in the characteristics of their surface(s). Such hydrophobic surfaces can serve as a site or sites that enhance the formation of (e.g., they serve as bilayer nucleation sites), and/or lipid adhesion sites such that the resulting lipid bilayer is more strongly tethered to a nanochannel's sidewall than that it would be without the presence of the nanomembrane(s). The use of encircling nanomembranes (i.e., ones forming a nanopore as described herein) can be particularly useful in supporting a given lipid bilayers formation and subsequent stabilization. In embodiments, it can be useful to cause the formation of more than one lipid bilayer in a given nanochannel using one or more nanomembranes.

Another general feature of these embodiments is that the electroactive tunable dimensionality of the sidewall nanomembrane(s) enables them to be modified such that it decreases the total surface area that must be spanned by a given lipid bilayer. Lipid bilayers of smaller surface areas are known to be more stable than larger ones, so enabling nanomembranes to be tuned to provide for just enough lipid bilayer surface area to be formed to support a given application promotes their overall utility.

Utilizing the dimensional tunable selection of a nanomembrane-supported lipid bilayer also has the utility of providing a size-selectivity for molecules that can be inserted in a given lipid bilayer. In such embodiments, nanomembranes, and particularly encircling nanomembrane that create a nanopore as described herein, can be formed such that they support and stabilize the formation of a size-restricted lipid bilayer for a surface area that allows for the insertion of only a small number, or even just one, membrane protein, into the bilayer. Non-limiting embodiments include lipid bilayer-stabilizing a nanomembrane nanopores formed to stabilize a lipid bilayer such that it is size-restricted so that just one membrane protein, for example but not limited to, protein porins, ion channels, or protein nanopores, can insert into the lipid bilayer.

In some embodiments, it can be useful to disrupt a given lipid bilayer formed in a nanomembrane(s) nanochannel. In embodiments, electrical stimuli can be applied to such a nanomembrane to depolymerize, polymerize and/or otherwise change its dimensionality such that the lipid bilayer is effectively disrupted. Electrochemical depolarization and chemical reactivity methods also can be used in embodiments to make a nanomembrane become too hydrophilic to support a bilayer by electrochemically shielding and/or reacting away the nanomembrane's hydrophobic surface. One or more primary and/or secondary electrodes in embodiments also can be subjected to imposed electrical stimuli such that a lipid bilayer is disrupted by the attraction, repulsion, and/or electrophoresis of charged molecules in a lipid bilayer. The electrophoretic methods described herein also can be utilized to push or pull apart a lipid bilayer by asserting electromotive force(s) on the charged molecules of, and around, the lipid bilayer. The instruments and methods to induce mechanical pressure and/or temperature changes described herein also can be used in embodiments to disrupt a given lipid bilayer. In addition, combinations of two or more of these methods, oscillating these methods over time, etc. can be utilized to disrupt a nanomembrane-stabilized lipid bilayer.

The functionality of a lipid bilayer and/or molecules contained within it for such embodiments can be evaluated directly by the apparatus and methods described herein. In one type of embodiment, the electrode circuitry for one or more primary and/or secondary electrodes can be configured to monitor changes in the electrochemical permeability, resistivity, etc. of the lipid bilayer and/or analytes therein, and/or the analytes passing through the lipid bilayer (as well as through protein nanopores therein). These electrode(s) measurements can include sensing through the nanomembrane itself via the primary electrode upon which the nanomembrane is deposited, and/or via one or more electrodes located elsewhere. In embodiments, the measurements made can include, but are not limited to, measurements such as current, resistance, voltage, and/or capacitance through the nanomembrane and/or at one or more of any sidewall, bottom, bias, primary, and/or secondary electrodes in the apparatus, and/or any combinations of the above. The monitoring of an accumulation of charged analytes, ions and/or any other constellation of analytes passing through a lipid bilayer, and/or through a protein nanopore within a lipid bilayer, can be made via one or more electrodes in that are possible in embodiments. In embodiments, monitoring also can be conducted via the reaction of analytes and/or any other constellation of molecules passing through a given lipid bilayer, and/or through a protein nanopore within a lipid bilayer, via the use of one or more electrode in the apparatus, and/or at a given nanomembrane.

One particular set of embodiments, but not limiting others, is to monitor the functionality of membrane proteins, including, but not limited to: porins, ion channels, protein nanopores, membrane proteins, membrane enzymes, membrane receptors, membrane channel proteins, membrane transport proteins, complexes with and by thereof, and combinations thereof. Several of these membrane proteins, such as the porins as ion channels, are well known to form pores through which ions can be restricted, gated, and/or allowed to pass from one side of a lipid bilayer to the other by opening and closing in a regulated manner in response to agonists and antagonists of their functionalities. In embodiments, one or more of these proteins can be inserted into a given nanomembrane-supported lipid bilayer. In particular, a nanomembrane which provides for a size-restricting lipid bilayer that generally prevents more than one of these membrane proteins to be inserted in the lipid bilayer is preferred. The functionality of membrane proteins such as the porins and ion channels can be tested by placing a given test molecule (e.g., a known or potential agonist and/or antagonist of the protein's functionality) into the solution 'above' a given protein inserted into a lipid-bearing nanomembrane. A change in the membrane protein's functionality is then measured by one of the analyte monitoring methods described herein. In particular embodiments, monitoring is carried out using the apparatus and methods for electrode-based ion flow analyte monitoring provided herein. The apparatus and methods described herein to create an ion funnel current/voltage that draws analytes to the protein in a lipid bilayer, and/or to further manipulate the flow of ions through the opened pores of these proteins also are embodiments. As one non-limiting example, the chloride/silver/silver chloride measuring system described herein can be utilized to monitor the flow of ionic materials in these embodiments, for example to monitor the opening and/or closing of a given protein nanopore under the influence of the presence of agonists and/or antagonists. Other non-limiting embodiments, though, include functionality assays for any other of the lipophilic molecules, membrane protein, and membrane protein complexes.

Another particular set of embodiments enables the application of nucleic acid sequencing. In these embodiments, a protein nanopore (for example, but not limited to α-hemolysin or *Mycobacterium smegmatis* porin A nanopores) is inserted into a given nanomembrane-stabilized lipid bilayer. A size-restricting lipid bilayer that generally prevents more than one of these membrane proteins to be inserted is preferred. Nucleic acids are then placed in the solution in the chamber(s) 'above' the nanopore(s) in the lipid bilayer. The nucleic acids can be single stranded DNA, or RNA, oligomers of any length. These nucleic acid oligomers may or may not contain naturally or artificially modified nucleotides (e.g., nucleic acids naturally modified such as containing 5-methylcytidine; nucleic acids artificially modified such as to insert spacers between the nucleotides and/or to modify the nucleic acid's bases with 'tags' to increase their bulk, and/or to modify their properties when monitored by any given sensor system, etc.). The nucleic acid oligomers also may be double stranded, or partially double stranded, oligomers of any length. In the instance of the oligomer being partially double stranded, such an oligomer can for example be formed by hybridizing a complementary nucleic acid oligomer of any length so long as it is sufficiently stable to maintain its double-stranded form in a useful manner for testing (e.g., complementary oligomers made of two nucleotides or longer and of know sequence are used in applications in the art to create partially double stranded oligomers). After adding the nucleic acid oligomer into the solution 'above' the protein nanopore, an ion funnel current/voltage as described herein can be initiated to cause the negatively charged nucleic acids to move towards, and eventually through, a given protein nanopore. Deriving the sequence of the nucleic acid as it passes through a given protein nanopore as it is residing in a nanomembrane-stabilized lipid bilayer can be carried out by several applications of the methods and apparatus described herein. Whatever mode is used to identify the oligomer's sequence, though, the overarching process of obtaining an oligomers sequence as it passes through a protein nanopore (or through a nanomembrane-encircled nanopore or suitable nanochannel), this process generally is described in the art as 'sequencing-by-threading' since it requires a given oligomer to be passed through a hole/pore that metaphorically is akin to passing a thread to the eye of a needle. In one set of embodiments, the flow of ions passing through the protein nanopore along with a nucleic acid oligomers is monitored using the apparatus and methods for electrode-based ion flow analyte monitoring through a nanomembrane nanopore as provided herein. A sequence is derived from these data by compiling the measured signals in comparison with the previously determined signals correlated to a given DNA or RNA nucleotide, or double-strand base pairs, or modified versions thereof, as they sequentially pass through a protein nanopore residing in a nanomembrane-stabilized lipid bilayer. A sequence also may be derived by monitoring the timing at which measured signals change as a partially double-stranded nucleic acids pass through such a protein nanopore. A sequence is derived from these data by compiling the measured signals in comparison with the signals previously correlated to single-versus double-stranded nucleic acids as they pass through a protein nanopore, knowledge of the sequence of the nucleic acid oligomer which was used to form the partial double-strands, and the timing between when the single versus double strand nucleic acid signals were measured. In another embodiment, the primary electrode(s) upon which the lipid bilayer-supporting nanomembrane is deposited can be used to monitor the passage of a nucleic acid through a given protein nanopore. In particular, the through-nanomembrane analyte monitoring apparatus and methods described herein can be used for these embodiments. Regardless of the signal monitoring method employed, though, nucleic acid sequencing can be carried out by compiling the measured signals of a nucleic acid's passage through a given protein nanopore in comparison with previously correlated signals determined for single- and/or double-stranded nucleic acids, and/or modified versions thereof. In other embodiments, the chloride/silver/silver chloride measuring system described herein can be utilized to monitor the flow of nucleic acid oligomers and chloride ions through a protein nanopore, and then derive the sequence of the oligomer by comparison to pre-characterized signals established for known nucleotides and/or groups of nucleotides.

In other embodiments, nanopores (i.e., nanomembrane-encircled nanochannels rather than one formed by a protein nanopore) can be utilized to enable nucleic acid sequencing. In these embodiments, a single nanopore is formed within a given nanotube or nanowell. Nucleic acid oligomers are placed in the solution in the chamber(s) 'above' the nanopore. The nucleic acids can be single stranded DNAs or RNAs oligomers of any length. These DNAs and/or RNAs may or may not contain naturally or artificially modified nucleotides (e.g., naturally modified such as 5-methylcytidine; artificially modified such as to insert spacers between the nucleotides, and/or modified with 'tags' to increase their bulk, and/or bearing any other type of modified nucleic acid bases such that they can be monitored by a given sensor system, etc). The nucleic acids also may be double stranded, or partially double stranded, oligomers of any length. For partially double stranded DNAs, these can be formed by hybridizing complementary nucleic acid oligomers of any length so long as they are sufficiently stable to maintain their partially double-stranded forms in a useful manner for testing (e.g., complementary oligomers of two or more nucleotides have been used in applications in the art to make partially double-stranded DNAs). The double-stranded or partially double-stranded DNA also may be naturally or artificially modified as with single-stranded DNAs or RNAs.

After placing the nucleic acids 'above' the nanopore, an ion funnel current/voltage can then be initiated to cause the negatively charged nucleic acids to move towards, and eventually through, the nanopore. FIGS. 4A and 4B summarize these processes, depicting the ion funnel current/voltage-induced flow of single-stranded and partially double-stranded nucleic acids through nanopores, respectively. Deriving the sequence of the nucleic acid that is moving through a nanopore can be carried out by several applications of the methods and apparatus described herein. In one set of embodiments, the flow of ions or ionic material passing through the nanopore along with a given nucleic acid is monitored using the apparatus and methods described herein to monitor the flow of ionic materials through nanomembrane nanochannels. A sequence is derived from these data by compiling the measured signals in comparison with the previously determined signals correlated to a given DNA or RNA nucleotide, or double-strand base pairs, or modified versions thereof, as they individually pass through a nanopore. A sequence also may be derived by monitoring the timing at which measured signals change as a partially double-stranded nucleic acids pass through a given nanopore. A sequence is derived from these data by compiling the measured signals in comparison with the signals previously correlated to single- versus double-stranded nucleic acids as they pass through a given nanopore, knowledge of the sequence of the nucleic acid oligomer which was used to form the partial double-strands, and the timing between when the single- versus double-strand nucleic acid signals were measured. In another embodiment of the apparatus and method, the primary electrode(s) upon which the nanopore is deposited can be used to monitor the passage of a nucleic acid through a given nanopore. In particular, the through-nanomembrane analyte monitoring apparatus and methods described herein can be useful for these embodiments. In some embodiments, one or more electrode above and below the general surface of the nanomembrane forming the nanopore can be used to monitor the passage of the nucleic acid, which may or may not be accompanied by other ionized molecules, through the nanopore. Regardless of the signal generation method employed, nucleic acid sequencing is carried out by compiling the measure signals of a nucleic acid's passage through a given nanopore in comparison with previously correlated signals determined for single- and/or double-stranded nucleic acids, and/or modified versions thereof. In other embodiments, the chloride/silver/silver chloride measuring system described herein can be utilized to monitor the flow of nucleic acid oligomers and chloride ions through a nanopore, and then derive the sequence of the oligomer by comparison to pre-characterized signals established for known nucleotides and/or groups of nucleotides.

In other embodiments, the nanomembrane portion of a given nanopore's outer perimeter can be functionalized via the attachment of, but not limited to, proteins, enzymes, antibodies, lectins, peptides, amino acids, modified amino acids, lipids, nucleic acids (single and double stranded DNAs, RNAs, aptamers), nucleic acid components (nucleosides, nucleotides, methylated/modified versions of the same), ionized salts, small molecules, drugs, etc., and combinations thereof. In particular, it can be useful to manufacture the nanomembrane as described herein such that the deposited material is in close proximity to where to the nanopore is positioned in a nanomembrane, and that this portion of the nanomembrane has chemical properties that are substantially different from the bulk of the rest of the nanomembrane. Thus, such embodiments provide for functionalization attachment sites that can be highly localized to the nanopore's nanomembrane rim, and/or sidewall.

Figure 5A:
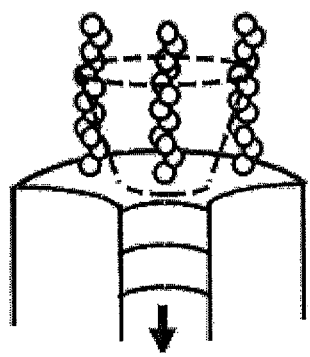
FIGS. 5A-5B depict exemplary embodiments in monitoring DNA hybridization.
Figure 5B:
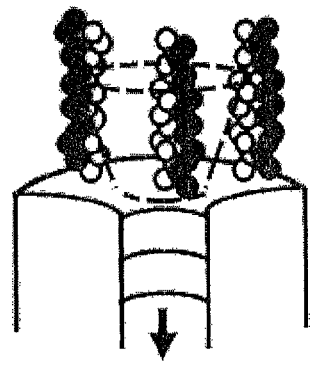
Figure 6A:
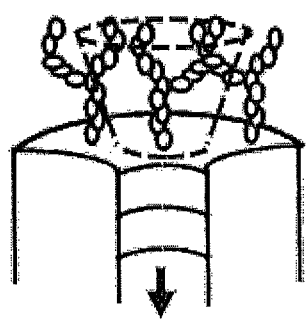
FIGS. 6A-6B depict exemplary embodiments in monitoring antigens binding to antibodies.
Figure 6B:
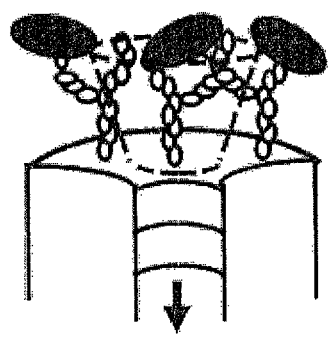

One non-limiting example of such embodiments is to add 'target' molecules that can interact, be bound by, be chemically reacted upon by, etc. by an appropriate functionalization on the nanomembrane forming, and in particular in close proximity to, a nanopore. Targets herein are defined as analytes that can be added over such a functionalized nanopore in solution and/or in gas phase and then specifically interact with a given type of nanomembrane functionalization. Examples of appropriate functionalizations and their 'targets' include, but are not limited to: enzymes and their substrates; antibodies/antibody fragments and their antigens; protein drug targets and their drugs; aptamers and their ligands; lectins and their carbohydrate ligands; metal chelators/binders and metal ions; single-stranded DNA oligomers and their complementary DNA oligomers; and RNAs and RNA binding proteins. Measurements of the flow of ionic materials, targets and other analytes added into the solution and/or gas placed 'above' a nanopore are then taken over time, particularly under the conditions of the formation of an ion funnel current/voltage as described herein, to monitor for signal changes resulting from an interaction between a given form of functionalization and its target. As one non-limiting example of this, FIGS. 5A and 5B depict the use of single-strand DNA-functionalized nanopore with an imposed ion funnel current/voltage, before and after complementary single-strand DNA binding. As another non-limiting example, FIGS. 6A and 6B depict the use of an antibody-functionalized nanopore with an imposed ion funnel current/voltage, before and after antigen binding. The means by which the interaction of a given 'target' and a nanopore's functionalization are monitored can include any appropriate method, or combination of methods, described herein for analyte flow monitoring. For example, embodiments to monitor for the resulting signal changes can include, but are not limited to, a decrease in the rate of flow of a given target through a nanopore, a decrease in the flow of accompanying ionic material and/or chemically reactive species through a nanopore, and/or an increase in the rate of flow of products resulting from an enzyme-catalyzed reaction through a nanopore. In other embodiments, the chloride/silver/silver chloride measuring system described herein can be utilized to monitor the flow of target(s) through the rim-functionalized nanopore, and then derive the sequence of the oligomer by comparison to pre-characterized signals established for a known target, and/or groups of targets.

In other embodiments, nanomembranes are formed via methods described herein such that a given nanopore is functionalized within its lateral-cross section (i.e., functionalization(s) are made to at least some portion of the encircling nanomembrane sidewall that forms a given nanopore). Examples of the methods for forming functionalization attachment surfaces (including, in particular, ones in which the attachment surfaces that are restricted in close proximity to a nanopore sidewall's outer perimeter), modes of functionalization, and functionalization types are as included herein. In these embodiments, a given 'target' of a functionalization type is provided in a solution or gas phase over the surface of a nanomembrane containing a nanopore. The means by which the interaction of this given 'target' and a nanopore's functionalization is monitored can include any appropriate method, or combination of methods, described herein for analyte monitoring. For example, embodiments to monitor for the resulting signal changes can include, but are not limited to, a decrease in the rate of flow of a given target through a nanopore, a decrease in the flow of ions through the nanopore, and an increase in the rate of flow of products resulting from an enzyme-catalyzed reaction through a nanopore. In other embodiments, the chloride/silver/silver chloride measuring system described herein can be utilized to monitor the flow of target(s) through the sidewall-functionalized nanopore, and then derive the sequence of the oligomer by comparison to pre-characterized signals established for a known target and/or groups of targets.

In other embodiments, a nanopore can be functionalized with nucleases, enzymes capable of cleaving DNAs and or RNAs into nucleotides, with the overarching application of enabling DNA and/or RNA oligomer sequencing. Examples of the methods for forming a nuclease attachment surface (including, in particular, ones in which the nuclease attachment surface is restricted in close proximity to a nanopore's outer perimeter), modes of nuclease functionalization, and nuclease functionalization types are as included herein. Both endo- and exonucleases can be utilized in embodiments, as well as can nucleases with specificities including single- and/or double-stranded DNAs and/or single-stranded RNAs and/or modified versions of the same. Nucleic acid oligomers can be single- and/or double-stranded DNAs, single-stranded RNAs, modified versions of the same as described herein, and can be oligomers of any length. For such embodiments, an ion funnel current/voltage is initiated and nucleic acid oligomers are placed in solution in the chamber(s) 'above' a nuclease-functionalized nanopore (FIGS. 3A-3C). The ion funnel current/voltage then causes the negatively charged nucleic acid oligomers to move towards a nanopore where one of the nucleases attached at its rim sequentially cleaves the oligomer into nucleotides (FIG. 3D). The nucleotides, which also are negatively charged, are drawn into/through the nanopore due the effects of the ion funnel current/voltage. Deriving the sequences of the nucleic acid oligomers can be carried out by several applications of the methods and apparatus described herein. Whatever mode is used to identify the oligomer's sequence, though, the overarching process of obtaining an oligomers sequence by identifying the nucleotides that result from an oligomer's cleavage is generally described in the art as 'sequencing-by-degradation.' In one set of embodiments, the nucleotides are directly sampled and the identified from material that is sequentially taken from the space below the nanopore (e.g., from samples taken from the space(s) 'below' the nanopore that are in the nanotube or nanowell in which they are formed and/or the chamber(s) below the nanotube's exit from its solid support). In another set of embodiments, the flow of the nuclease-cleaved nucleotides ions passing through the nanopore is monitored using the apparatus and methods for ionic analyte movement monitoring over nanomembranes as provided herein. For example, in embodiments, one or more electrodes above and below the general surface of the nanomembrane forming the nanopore are used to monitor the passage of the ionized nucleotides, and/or the flow of other ionized analytes that can be in motion with the nucleotides, which may or may not be accompanied by other ionized molecules, through the nanopore. A sequence is derived from these data by compiling the measured signals of the moving ionized nucleotides, and/or other ionized molecules in motion with the nucleotides, in comparison with the previously determined signals correlated to a given DNA or RNA nucleotide. In another embodiments, the primary electrode(s) upon which a given nanopore is deposited can be used to monitor the passage of nucleotides through a given nanopore. In particular, the through-nanomembrane analyte monitoring apparatus and methods appropriate for monitoring nucleotides and as described herein can be particularly useful for these embodiments. In particular, it can be useful to employ methods in which electrical stimuli is applied to an electrically conductive nanomembrane and then measurements such as capacitance, current, voltage, etc. are taken at one or more secondary electrodes that form one or more other portions of a nanopore's cross-section, or are taken at one or more secondary electrodes above or below the nanopore's cross-section. In any case, nucleic acid oligomer sequences are derived by compiling the measure signals of the nucleotides' passage through a given nanopore in comparison with previously correlated signals determined for single- and/or double-stranded nucleotides, and/or modified versions thereof. In other embodiments, the chloride/silver/silver chloride measuring system described herein can be utilized to monitor the flow of nucleotides and chloride ions through a nanopore, and then derive the sequence of the oligomer by comparison to pre-characterized signals established for known nucleotides and/or groups of nucleotides.

In embodiments, a suitable nanochannel within a nanomembrane (i.e., a nanochannel that is not entirely encircled by nanomembrane as is defined herein as being a nanopore) can be used in place of a nanopore for many the applications just described. Suitable nanochannels can include, but are not limited to, ones that provide for functionalization sites, if required, that can be highly localized to nanochannel's nanomembrane rim. Nanochannels also can include ones that have at least some portion of their sidewall defined by the placement of a nanomembrane(s) such that a required through-nanomembrane monitoring capabilities can be enabled. Nanochannels that are nearly encircled by deposited nanomembrane also can be useful since the electroactivity of the nanomembrane can be employed as required to tunably decrease the cross-section area through which a given analyte moves. Lowering the cross-section area has been described as helping to improve the signal-to-noise monitoring of analytes like nucleic acids as they move through protein nanopores (Clark et al., Nat. Nanotechnol 2009).

In embodiments, an imposed ion funnel current/voltage is applied to a solution containing double-stranded DNA that has been placed over a nuclease-functionalized nanopore or suitable nanochannel. However, instead of the nucleotides being drawn through the nanopore to enable the sequence determinations, the single-stranded DNA that is the other product of the nuclease reaction is caused to 'thread' through the nanopore or suitable nanochannel. The modes for sequencing the single-stranded DNA oligomer as it threads through a nanopore or suitable nanochannel are as is described previous embodiments.

Note that conventional sequencing-by-synthesis modes only provide for quite short oligomer sequence thread lengths. For example, current commercialized high-throughput DNA sequencing technologies that employ a DNA polymerase or DNA ligase to generate a sequencing signal by elongating the copy-strand of a DNA oligomer rarely provided accurate read lengths in excess of a few hundred bases. Such short read lengths greatly complicate the speed, accuracy, and cost of aligning the resulting data to provide for a high accuracy full-genome sequence map. The disclosed apparatus and methods provided herein for both the sequencing-by-threading and sequencing-by-degradation modes solve this problem. For example, the read lengths that can be derived from the sequencing-by-threading process described herein can be as long as the threaded oligomers themselves. Since it easily is possible to prepare samples of nucleic acid oligomers in excess of tens, or even hundreds of thousands, of bases in length, it can be possible to obtain read lengths that are orders of magnitude greater than is possible for sequencing-by-synthesis processes. Similarly, for the sequencing apparatus and methods mediated via sequencing-by-degradation described herein, the nuclease cleavage reactions underlying theses technologies are well known to be highly processive in that they generally continue to sequentially cleave a given nucleic acid oligomer until the end of the oligomer is reached, and regardless of the oligomers length. Thus, the sequencing-by-degradation apparatus and methods described herein therefore can provide read lengths that may be limited only by the lengths of the oligomers placed in a given sequencing sample. Hence, the apparatus and methods provided herein for sequencing-by-degradation can provide read lengths that are orders of magnitudes greater than what is possible for current commercialized sequencing-by-degradation technologies.

Furthermore, the apparatus and methods provided herein provide direct sequencing-by-threading and/or sequencing-by-degradation of RNA oligomers in modes that do not necessarily require the use of reverse transcriptases to convert these RNA oligomers into cDNAs. Reverse transcriptases are well known to introduce errors and increase the cost for RNA sequencing. In addition, it can be difficult and costly to sequence biologically important but inherently short oligomer RNA oligomers like those of the miRNAs via current sequencing methods. Thus, the apparatus and methods provided herein can greatly decrease the cost and increase the accuracy of RNA oligomer sequencing.

FIGS. 3A-3D depict analyte motion-inducing methods using devices of FIGS. 1 and/or 2A through 2C according to various embodiments of the present teachings. The analyte 366 can be induced to move across a given nanowell (see FIG. 1) and/or a given nanomembrane deposited within a nanowell (see FIGS. 2A-2C, or FIG. 3A) by subjecting a passive Brownian motion-driven diffusion movements, an electrophoretic force, and/or a mechanical pressure. In an exemplary embodiment, imposed electrical stimuli create an "ion funnel current/voltage" 370 to move the analyte 366.

FIGS. 4A-4B depict an exemplary embodiment of nucleic acid sequencing for a single-stranded nucleic acid 466 or a single-stranded nucleic acid 466 with partially double-stranded nucleic acid 469 through a nanopore or a suitable nanochannel. DNA and RNA threading through nanopore or suitable nanochannel can be conducted by positional sequencing using partially double-stranded DNAs. FIGS. 5A-5B depict an exemplary embodiment in monitoring DNA hybridization; while FIGS. 6A-6B depict an exemplary embodiment in monitoring antigens binding to antibodies.

Employing that the nanotechnologies and their compatibility to standard silicon manufacturing processes, the present disclosure makes it possible to form cost-effective hand-held analyte detectors and/or to carry out parallel analyte detection reactions in a server blade-style format such that scaling for two or more simultaneous independent detection can be carried out. The analytes detected need not be the same in such parallel operations. While during and/or after a given analyte detection reaction is carried out, all of the resulting data can be communicated by wires (standards such as ethernet, usb, or dial-up) or wirelessly (standards such as zigbee, Bluetooth, wifi, WiMax, citizens band, satellite link, or cell phone formats) or combinations thereof (standards such as wireless connection to land line-based communications links).

As disclosed, nanopores and/or nanochannels formed by electroactive nanomembrane(s) can have an electrically tunable diameter as a result from an electroactive response of the nanomembranes. In embodiments, insulating layers, such as for example, a metal oxide, glasses, nonconductive polymers, and/or silicon, can be included to form the nanopores/nanochannels. For example, alternating layers of an electroactive nanomembrane and an insulating material can be formed on at least one electrode of a nanotube or a nanowell. The alternating layers can be formed by, e.g., the disclosed electrochemical deposition, and other methods such as energetic neutral beam lithography/epitaxy. In some embodiments, a place holder or a template can be placed within a corresponding nanotube or nanowell during deposition of nanomembranes and then removed from the deposited nanomembranes leaving a nanopore or a nanochannel formed by the deposited one or more nanomembranes. For example, the place holder/template can be a cylinder or a strip formed by, e.g., photocurable polymer. In another example, the insulating layer can be deposited over the electroactive nanomembrane but expose an edge of the nanomembrane for further deposition of, e.g., a polymer, on the edge. In other embodiments, nanopores, nanochannels can be formed by first depositing nanomembranes to fill nanotubes/nanowells and then drilling openings through the nanomembranes, e.g., using a focused ion beam.

In embodiments, nanopores or nanochannels can be used for treating an analyte molecule or control flow of a fluid. For example, a sensor structure or a flow controlling structure can be formed by using a separation structure, which can be the disclosed device including nanomembranes deposited in nanowells/nanotubes in a support material. The separation structure can separate a sample chamber from a collection chamber such that analyte molecules or other molecules or the fluid can move from the sample chamber through nanopores/nanochannels and into the collection chamber. The sensor structure can further include a first electrode pair having electrodes disposed at opposite ends (e.g., including the bottom electrode) of the electroactive nanopore/nanochannel. The sensor structure can also include a second electrode pair (e.g., including sidewall electrodes) disposed in the sidewall of nanowells/nanotubes between the first electrode pair. The nanomembranes can be disposed over at least one electrode of the second electrode pair.

In operation, a first electrical stimuli that are sufficient to cause the analyte molecule or other molecules or the fluid to migrate from the sampling chamber through the electroactive nanopores/nanochannels to the collection chamber can be applied across the first electrode pair. When analyte molecules or the fluid in the sampling chamber pass through the electroactive nanopores/nanochannels, a current across the first electrode pair, e.g., indicative of the presence of the analyte molecule, can be measured. The diameter of the nanopores/nanochannels formed by the electroactive membrane(s) can be electrically tuned (i.e., increased or decreased) by applying a second electrical stimuli across the second electrode pair, which causes the electroactive membrane(s) to either expand or contract. In embodiments, a flow of an ionic species can also be controlled through the nanopores/nanochannels, e.g., by attracting the ionic species using an ion funnel current/voltage through the opening of the nanopores/nanochannels and tuning (increasing or decreasing) the electrically tunable diameter of the opening so as to control flow of the ionic species through the nanopores/nanochannels.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device comprising:
one or more nanowells disposed within a support material, each nanowell comprising one or more sidewall electrodes or one or more bottom electrodes;
one or more electroactive nanomembranes disposed on at least a portion of the one or more sidewall electrodes or on at least a portion of the one or more bottom electrode; and
a lipid bilayer disposed on the one or more electroactive nanomembranes, wherein the lipid bilayer is configured to allow insertion of a molecule;
a nanochannel or nanopore formed by the one or more electroactive nanomembranes to support or stabilize the lipid bilayer;
wherein the one or more electroactive nanomembranes change dimension in response to an electrical stimulus applied to the one or more sidewall electrodes or the one or more bottom electrodes;
wherein a surface area spanned by the lipid bilayer is limited by the one or more electroactive nanomembranes such that only one of the molecule may be inserted into the lipid bilayer,
wherein the one or more electroactive nanomembranes encircle the lipid bilayer.

2. The device of claim 1, wherein the lipid bilayer is configured to provide insertion and functionality testing of one or more lipophilic molecules comprising detergents, oils, fats, lipids, surfactants, or combinations thereof, or proteins comprising porins, ion channels, protein nanopores, membrane proteins, membrane enzymes, membrane receptors, membrane channel proteins, membrane transport proteins, complexes with and by thereof, or combinations thereof, and wherein the insertion comprises an insertion of one molecule of protein.

3. The device of claim 1, wherein the one or more electroactive nanomembranes have a hydrophobic surface as a nucleation site or an adhesion site configured to promote nucleation of formation or stabilization of a lipid bilayer.

4. The device of claim 1, wherein the one or more electroactive nanomembranes comprise a hydrophobic surface is configured to allow nucleation of formation of the lipid bilayer or to stabilize the lipid bilayer.

5. The device of claim 1, wherein the one or more sidewall electrodes or the one or more bottom electrodes are exposed to an interior of the nanowells.

6. The device of claim 1, further comprising another nanomembrane of a distinct property from the one or more electroactive nanomembranes, wherein the other nanomembrane is disposed on the one or more electrodes.

7. The device of claim 1, wherein the nanomembrane is electrically conductive.

8. The device of claim 1, wherein the one or more electroactive nanomembranes comprises an electroactive polymer.

9. A device comprising:
one or more nanotubes disposed within a support material, each nanotube comprising one or more sidewall electrodes;
one or more electroactive nanomembranes disposed on at least a portion of the one or more sidewall electrodes of the one or more nanotubes; and a lipid bilayer disposed on the one or more electroactive nanomembranes, wherein the lipid bilayer is configured to allow insertion of a molecule;

a nanochannel or nanopore formed by the one or more electroactive nanomembranes to support or stabilize the lipid bilayer;

wherein the one or more electroactive nanomembranes change dimension in response to an electrical stimulus applied to the one or more sidewall electrodes;

wherein a surface area spanned by the lipid bilayer is limited by the one or more electroactive nanomembranes such that only one of the molecule may be inserted into the lipid bilayer;

wherein the one or more electroactive nanomembranes encircle the lipid bilayer.

10. The device of claim 9, wherein the lipid bilayer is configured to provide insertion and functionality testing of one or more lipophilic molecules comprising detergents, oils, fats, lipids, surfactants, or combinations thereof, or proteins comprising porins, ion channels, protein nanopores, membrane proteins, membrane enzymes, membrane receptors, membrane channel proteins, membrane transport proteins, complexes with and by thereof, or combinations thereof, and wherein the insertion comprises an insertion of one molecule of protein.

11. The device of claim 9, wherein the one or more electroactive nanomembranes have a hydrophobic surface as a nucleation site or an adhesion site configured to promote nucleation of formation or stabilization of a lipid bilayer.

12. The device of claim 9, wherein the one or more electroactive nanomembranes comprise a hydrophobic surface is configured to allow nucleation of formation of the lipid bilayer or to stabilize the lipid bilayer.

13. The device of claim 9, wherein the one or more sidewall electrodes are exposed to an interior of the nanotubes.

14. The device of claim 9, further comprising another nanomembrane of a distinct property from the one or more electroactive nanomembranes, wherein the other nanomembrane is disposed on the one or more electrodes.

15. The device of claim 9, wherein the nanomembrane is electrically conductive.

16. The device of claim 9, wherein the one or more electroactive nanomembranes comprises an electroactive polymer.

* * * * *